US010451634B2

(12) United States Patent
Krishna et al.

(10) Patent No.: US 10,451,634 B2
(45) Date of Patent: Oct. 22, 2019

(54) METHOD OF USING HUMAN FC-BEARING IGG ANTIBODIES TO POLYETHYLENE GLYCOL

(71) Applicant: BRISTOL-MYERS SQUIBB COMPANY, Princeton, NJ (US)

(72) Inventors: Murli Krishna, Yardley, PA (US); Alexander T. Kozhich, Princeton, NJ (US); Martin J. Corbett, Mount Holly, NJ (US); Zheng Lin, North Wales, PA (US); Steven P. Piccoli, Princeton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 15/720,073

(22) Filed: Sep. 29, 2017

(65) Prior Publication Data

US 2018/0038872 A1 Feb. 8, 2018

Related U.S. Application Data

(62) Division of application No. 15/018,353, filed on Feb. 8, 2016, now Pat. No. 9,804,170.

(60) Provisional application No. 62/113,733, filed on Feb. 9, 2015.

(51) Int. Cl.

*G01N 33/53* (2006.01)
*G01N 33/68* (2006.01)
*C07K 16/44* (2006.01)

(52) U.S. Cl.

CPC ......... *G01N 33/6854* (2013.01); *C07K 16/44* (2013.01); *C07K 2317/24* (2013.01); *G01N 2800/52* (2013.01)

(58) Field of Classification Search

CPC ................................................. G01N 33/6854

See application file for complete search history.

(56) References Cited

U.S. PATENT DOCUMENTS

| | | | |
|---|---|---|---|
| 8,785,139 | B2 | 7/2014 | Weber et al. |
| 2012/0015380 | A1 | 1/2012 | Cheng et al. |

FOREIGN PATENT DOCUMENTS

| | | | |
|---|---|---|---|
| WO | WO 2002/094853 A2 | 11/2002 | |
| WO | WO 2008/063663 A2 | 5/2008 | |
| WO | WO 2010/088547 A1 | 8/2010 | |

OTHER PUBLICATIONS

Rudikoff et al. Proc. Natl. Acad. Sci. USA vol. 79, pp. 1979-1983 (Mar. 1982).*

Janeway et al. Immunology, 3rd ed., 1997, Garland Publications, Inc., pp. 3:1-3:11.*

Keguan Chen et al., *Journal of Immunological Methods*, "False-Positive Immunogenicity Responses Are Caused by CD20 B Cell Membrane Fragments in an Anti-Ofatumumab Antibody Bridging Assay", vol. 394: pp. 22-31, 2013.

Tian-Lu Cheng et al., *Bioconjugate Chem*, "Monoclonal Antibody-Based Quantitation of Poly(Ethylene glycol)-Derivatized Proteins, Liposomes, and Nanoparticles", vol. 16, pp. 1225-1231 , 2005.

Huijin Dong et al, *AAPS Journal*, "Development of Generic Anti-PEG Antibody Assay Using BioScale's Acoustic Membrane Micro Particle Technology", vol. 17, No. 6, pp. 1511-1516, Nov. 2015.

Michael S. Hershfield, *Arthritis Research & Therapy.*, "Induced and Pre-Existing Anti-Polyethylene Glycol Antibody in a Trial of Every 3-Week Dosing of Pegloticase for Refractory Gout, Including in Organ Transplant Recipients", vol. 16: R63, pp. 01-11, 2014.

Murli Krishna et al., *Bioanalysis*, "Development and Characterization of Antibody Reagents to Assess Anti-PEG IgG Antibodies in Clinical Samples", vol. 07: No. 15, pp. 1869-1883, 2015.

Yijuan Liu et al., *Journal of Parmacological and Toxicological Methods.*, "A Double Antigen Bridging Immunogenicity ELISA for the Detection of Antibodies to Polyethylene Glycol Polymers", vol. 64: pp. 238-245, 2011.

Heather Myler et al., *Bioanalysis*, "Anti-PEG Antibody Bioanalysis: A Clinical Case Study With PEG-IFN λ-1a and PEG-IFN α2a in Naïve Patients", vol. 07: pp. 1093-1106, 2015.

Mark G.P. Saifer et al, *Molecular Immunology*, "Selectivity of Binding of PEGs and PEG-Like Oligomers to Anti-PEG Antibodies Induced by MethoxyPEG-Proteins", vol. 57, pp. 236-246, 2014.

Merry R. Sherman, *Bioconjugaste Chemistry*, "Role of the Methoxy Group in Immune Responses to mPEG-Protein Conjugates", vol. 23: pp. 485-499, 2012.

Yu-Cheng Su et al, *Bioconjugate Chemistry*, "Sensitive Quantification of PEGylated Compounds by Second-Generation Anti-Poly (Ethylen Glycol) Monoclonal Antibodies", vol. 21, pp. 1264-1270, 2010.

William Weaver et al,"Evaluation and Optimization of a Commercial ELISA Kit for the Detection of Antibodies to Polyethylene Glycol (PEG) in Human Serum for Use in Support of Clinical Studies for PeGylated Therapeutic Drug", Presented at the 2012 AAPS Annual Meeting and Exposition, Chicago, Illinois, Oct. 14-18, 2012.

David A. Wunderlich et al., *Hybridoma*, "Generation and Characterization of a Monoclonal IgG Antibody to Polyethylene Glycol", vol. 26: No. 03, pp. 168-172, 2007.

(Continued)

*Primary Examiner* — Prema M Mertz

(74) *Attorney, Agent, or Firm* — Gregory R. Bellomy

(57) ABSTRACT

Polyethylene glycol (PEG) is often conjugated with therapeutic proteins to enhance their PK properties. PEG may, however, be immunogenic, and the presence of PEG in food and cosmetics is believed to result in pre-existing anti-PEG antibodies in humans. Polyclonal and monoclonal antibodies reactive to PEG are provided for use in immunogenicity assay development to detect such anti-drug antibodies. Such antibodies exhibit preferential binding based on the size of PEG with molecular weight ranging from 350 daltons to 40 kD. Anti-PEG antibodies of the invention are engineered to comprise human Fc regions to enable non-bridging immunoassay formats.

9 Claims, 14 Drawing Sheets

Specification includes a Sequence Listing.

(56) References Cited

OTHER PUBLICATIONS

ANP Technologies, Inc., Antibodies, pp. 1-4, http://www.anptinc.com/#!antibodies/k07lk May 16, 2016.
IBMS Academica Sinica, Anti-PEG Antibodies http://www.ibms.sinica.edu.tw/~sroff/anti-peg/, May 16, 2016.
Gene Tex, Anti-PEG Antibody, http://www.biovision.com/anti-peg-antibody-clone-09f02-6162.html , May 16, 2016.
BioVision, Anti-PEG Antibody (clone 09F02), http://biovision.com/anti-peg-antibody-clone-09f02-6162.html, May 16, 2016.
Epitomics, Anti-PEG Antibodies, High Affinity Rabbit Monoclonal Antibodies, www.epitomics.com/pdf/anti_PEG_v2.pdf, May 16, 2016.
Life Diagnostics, Inc. PEG Antibodies, http://lifediagnostics.com/peg-reagents/peg-antibodies/, May 16, 2016.
Maine Biotechnology Services, PEG Antibody, http://mainebiotechnology.com/product-search/peg-antibody/, May 16, 2016.
Abnova, Polyethylene Glycol Matched Antibody PAIR, http://www.abnova.com/images/content/support/peg%20matched%20ab20pair.pdf, May 16, 2016.
GenScript, The PEG Antibody (Biotin), mab, Mouse, http://www.genscript.com/antibody/A0176_100-he_sup_TM_sup_PEG_Antibody_Biotin_mAb_Mouse.html, May 16, 2016.

* cited by examiner

FIG. 1B

Biotin-PEG conjugates

Mono-methyl triethylene glycol (mTEG) $CH_3O$ - $(CH_2CH_2O)_3$ H

Amine – PEG – amine (aPEGa) $H_2N$ -O $(CH_2CH_2O)_n$ - $NH_2$

METHOD OF USING HUMAN FC-BEARING IGG ANTIBODIES TO POLYETHYLENE GLYCOL

CROSS-REFERENCE TO RELATED APPLICATIONS

This application is a divisional of co-pending U.S. patent application Ser. No. 15/018,353, filed Feb. 8, 2016, which claims the benefit under 35 U.S.C. § 119(e) of U.S. Provisional Application No. 62/113,733, filed Feb. 9, 2015, the disclosures of which are incorporated herein by reference.

SEQUENCE LISTING

Incorporated herein by reference in its entirety is a Sequence Listing named "SEQT_12462USNP.txt," comprising SEQ ID NO:1 through SEQ ID NO:14, which include nucleic acid and/or amino acid sequences disclosed herein. The Sequence Listing has been submitted herewith in ASCII text format via EFS-Web, and thus constitutes both the paper and computer readable form thereof. The Sequence Listing was first created using PatentIn 3.5 on Feb. 4, 2016, and is approximately 23 KB in size.

BACKGROUND

Polyethylene glycol (PEG) is a polymer that is commonly used as a covalent adduct to many biotherapeutic agents to increase their circulatory half life. By increasing the hydrodynamic radius of the molecule, PEG reduces loss due to glomerular filtration and leading 12 to decreased renal clearance. Kang et al. (2009) *Expert Opin. Emerg. Drugs* 14:363; Fishburn et al. (2008) *J. Pharm. Sci.* 97:4167. The PEG moiety on the therapeutic may vary in length (20 to 40 kD) and in branching.

PEG is also known to be ubiquitously present in food and cosmetic products to which human exposure is believed to elicit anti-PEG antibodies. Hershfield et al. (2014) *Arthritis Res. Ther.* 16:R63; Schellekens et al. (2013) *Pharm. Res.* 30:1729; Garay et al. (2012) *Expert Opin. Drug Deliv.* 9:1319. The PEG in such products is generally smaller and simpler in structure than PEG that is linked to a protein therapeutic.

Immunogenicity of biotherapeutics is known to influence their bioavailability, in vivo pharmacological potency, and immune complex mediated adverse effects. Gorovits et al. (2014) *J. Immunol. Methods* 408:1. Although PEG has been considered to be of low immunogenic risk due to its simple subunit repeat structure and low charge density, there have been several reports documenting both pre-existing anti-PEG antibodies in humans as well as therapeutic induced anti-PEG antibody response. Armstrong et al. (2007) *Cancer* 110:103; Hershfield et al. (2014) *Arthritis Res. Ther.* 16:R63; Ganson et al. (2006) *Arthritis Res Ther.* 8:R12. In some instances drug induced anti-PEG antibodies have been shown to increase the clearance of a PEGylated enzyme therapeutic. Armstrong et al. (2007) *Cancer* 110:103. Several groups have also raised both IgM and IgG antibodies against PEG in mice. Cheng et al. (2005) *Bioconjug. Chem.* 16(5):1225; Su et al. (2010) *Bioconjug. Chem.* 21:1264.

Most immunogenicity assays developed for a PEGylated therapeutic protein determine anti-drug antibody (ADA) response to the whole drug without discriminating between the specificity of the ADA towards the protein and PEG components of the therapeutic molecule. Some groups have addressed these questions by using PEG as a competitor in the ADA assay. Liu et al. (2011) *J. Pharmacol. Toxicol. Methods* 64:238; Hershfield et al. (2014) *Arthritis Res. Ther.* 16:R63. Others have used a separate bridging assay that uses an IgM anti-PEG positive control, but such an assay would only detect an IgM response. That most pre-existing anti-PEG antibodies might be IgM might make such an assay relevant. However, it is conceivable that antibodies induced by sustained chronic exposure to a PEGylated therapeutic, or food and cosmetic additives, might mature to an IgG isotype and would not be detected in an IgM bridging assay. Depending on the patient's immune status and the therapeutic indication, ADA of all isotypes specific to PEG may be relevant to drug safety in humans and therefore need to be monitored.

Our work has led to the realization that an ideal assay to detect such anti-PEG ADA would be (a) capable of detecting anti-PEG antibodies of wide range of affinities, with a broad specificity across all PEG sizes and shapes (b) a generic assay suitable for any PEGylated therapeutic drug regardless of the underlying protein portion of the drug and (c) and capable of identifying antibodies of all isotypes (IgM and IgG). See, e.g., Myler et al. (2015) *Bioanalysis* 7:1093. We also realized that the multiplicity of the epitopes on the PEG backbone might preclude IgG anti-PEG ADA detection in the traditional bridging assay format by virtue of intra-chain binding rather than inter-chain bridging between molecules. Binding of both arms of an IgG anti-PEG to the same PEG chain would preclude use of a bridging assay, and necessitate a direct assay format involving detection of the Fc region of the antibody. In such assays the Fc in positive controls and experimental samples will need to be of the same species. Such analytical requirements need a panel of well characterized anti-PEG reagents preferably with a human IgG Fc.

The need exists for improved reagents for analytical experiments to characterize PEGylated molecules, such as PEGylated therapeutic molecules, including but not limited to PEGylated proteins, antibodies, or biologically active fragments thereof. Such reagents would ideally allow for detection, and optionally quantification, of such PEGylated molecules or free PEG in biological samples or tissues in a variety of applications besides immunoassays. Such improved reagents would simplify experimental design, improve precision and enable detection of IgG antibodies.

SUMMARY OF THE INVENTION

The present invention provides improved reagents for use in assays to detect anti-PEG antibodies in human subjects, e.g. anti-drug antibodies to PEGylated drugs, and related methods. Specifically, the antibodies and methods of the present invention allow for development and validation of assays for detection of human IgG anti-PEG antibodies that might otherwise be missed in bridging assays. Related methods of treatment, patient selection and therapeutic monitoring are also provided.

Anti-PEG antibodies of the present invention will typically comprise a human IgG Fc region for use in direct anti-drug antibody assays using human IgG Fc detection reagents, such as labeled anti-human IgG Fc antibodies.

In one embodiment the invention provides chimeric anti-PEG antibodies comprising non-human, e.g. mouse, variable domains and human IgG constant domains. Such antibodies may comprise the heavy chain complementarity determining regions (CDRs) of antibodies PEG.2 or PEG.1 disclosed herein, i.e. CDRH1, CDRH2, CDRH3 of mAb PEG.2 (residues 31-35, 50-68 and 101-109, respectively, of SEQ ID NO: 2) or CDRH1, CDRH2, CDRH3 of mAb PEG.1 (residues 31-35, 50-66 and 99-110, respectively, of SEQ ID NO: 6), and the light chain CDRs of antibodies PEG.2 and PEG.1 (variants a and b), i.e. CDRL1, CDRL2, CDRL3 of mAb PEG.2 (residues 31-37, 50-56 and 89-102, respectively, of SEQ ID NO: 4); CDRL1, CDRL2, CDRL3 of mAb PEG.1a (residues 24-34, 50-56 and 89-102, respectively, of SEQ ID NO: 8); or CDRL1, CDRL2, CDRL3 of mAb PEG.1b (residues 24-39, 55-61 and 94-102, respectively, of SEQ ID NO: 10).

Alternatively, anti-PEG antibodies of the present invention may comprise the sequences of the heavy and light chain variable domains (SEQ ID NOs: 2, 4, 6, 8 and 10), or full-length heavy and light chains (SEQ ID NOs: 11-14) of mAbs PEG.2 and PEG.1 (light chain variants a and b), as listed in Table 3.

Anti-PEG antibodies of the present invention may also comprise antibodies having at least 95% sequence identity with the CDRs, variable domains, and full-length heavy and light chain sequences of PEG.1 or PEG.2, and that retain the ability to bind to PEG. Antibodies having at least 95% sequence identity with the CDRs or variable domains of antibodies PEG.2 and PEG.1 may further comprise human IgG constant domains.

In other embodiment, antibodies of the present invention comprise anti-PEG antibodies that compete for binding with monoclonal antibodies PEG.2 or PEG.1, or polyclonal human antibody #2026, for binding to PEG. Such competing antibodies may further comprise human IgG constant domains.

In other embodiments, anti-PEG antibodies of the present invention comprise variable domains derived from the same mouse heavy chain germline sequences as antibodies PEG.2 and PEG.1 disclosed herein, i.e. V domain 3-11, D domain 4-17, and J domain JH4a or Jh4d. The anti-PEG antibodies may also comprise variable domains derived from the same mouse light chain germline sequences as antibodies PEG.2 and PEG.1, i.e. V domain A21 or A17 and J domain JK1 or JK2.

The present invention also provides polyclonal human anti-PEG antibodies obtained from transchromosomal cows, including human IgG anti-PEG antibodies, including antibodies comprising human heavy chains and at least one bovine light chain. One such antibody is referred to as pAb #2026. The invention further provides antibodies that compete with pAb #2026 for binding to PEG.

In another aspect the invention provides anti-PEG antibodies of the present invention further comprising a detectable label.

The invention further provides method of validating an anti-drug antibody assay for PEGylated drugs using one or more antibodies of the present invention as positive controls, either in creating a standard curve in parallel experiments or as internal standards added to experimental samples. In some embodiments, the anti-drug assay of the present invention involves exposing a sample from a human subject to a surface comprising immobilized PEG, washing, and then detecting the presence, absence or amount of anti-PEG antibody bound to the surface, e.g. using a detection reagent that selectively binds to the human IgG Fc.

In another embodiment the anti-PEG antibodies of the present invention are used as positive controls to create a standard curve comprising one or more data points in which a known concentration of the positive control antibody are used in the anti-drug antibody assay and an output signal is determined for each concentration. This standard curve can be used to determine the titer of human anti-PEG IgG present in a sample from a human subject by comparing the output signal of the assay with the values obtained using the positive control antibody or antibodies. In some embodiments only a single concentration of positive control antibody is used, whereas in other embodiments a series of concentrations is used. Standard curves based on a single concentration will typically find use in qualitative determination of the presence or absence of anti-PEG antibodies in a sample, whereas standard curves based on a series of concentrations may be used to calculate the titer of anti-PEG antibodies in the sample in a semi-quantitative manner.

Another embodiment of the present invention is a method of detecting human IgG anti-PEG antibodies in a sample by exposing a sample from a human subject to a PEG-coated surface, washing, and detecting the presence of human IgG anti-PEG antibodies bound to the surface, wherein the method further comprises comparing the results of the detection with the results obtained using positive control human IgG anti-PEG antibody or antibodies of the present invention to confirm the presence, absence, and optionally the approximate titer, of human IgG anti-PEG antibodies in the sample.

In another aspect, the invention provides methods of treatment of human subject with PEGylated therapeutic compounds comprising detecting human IgG anti-PEG antibodies in a sample obtained from human subjects treated with a PEGylated therapeutic compound, determining the titer of anti-PEG antibodies (ADA) by comparing results of this detection with a standard curve obtained using human IgG anti-PEG antibodies of the present invention as a positive control, and modifying the treatment regimen based on the presence, absence or titer of human IgG anti-PEG antibodies detected in the assay. Alternatively, the method may comprise obtaining a sample from the subject for detection of anti-drug antibodies (or requesting that such a sample be obtained); requesting that the titer of anti-PEG antibodies in the sample be determined, wherein the titer is determined with reference to a standard curve obtained using human IgG anti-PEG antibodies of the present invention as a positive control; and modifying the treatment regimen based on the presence, absence or titer of human IgG anti-PEG antibodies detected in the assay. In some embodiments, modifications of the treatment regimen include reducing dose or discontinuing therapy with the PEGylated drug if anti-drug antibodies might cause an adverse immune response in the subject, or increasing the dose of the PEGylated drug if the anti-drug antibodies merely reduce the efficacy of the PEGylated drug. In another embodiment, addition medications are administered to ameliorate unwanted side effects that might be caused by anti-drug antibodies.

In a further embodiment subjects may be excluded from therapy with a PEGylated therapeutic compound based on the presence, or level, of anti-PEG antibodies present prior to therapy, to avoid any unacceptable side effects. In another embodiment, the dose of PEGylated therapeutic compound is increased if anti-PEG antibodies are found prior to treatment to overcome any reduction in efficacy they might cause.

In various embodiments the therapeutic regimen for the subject is altered depending on whether the level of anti-PEG (anti-drug) antibodies is above a threshold level or not. This threshold level is determined on a case-by-case basis and is within the skill in the art for medical practitioners, and may be based on the level of anti-PEG antibody expected to render treatment ineffective, or the level of anti-PEG antibody likely to cause side effects that outweigh the benefits of treatment with the PEGylated therapeutic compound.

Other features and advantages of the instant disclosure will be apparent from the following detailed description and examples, which should not be construed as limiting.

BRIEF DESCRIPTION OF THE DRAWINGS

Figure 1B:
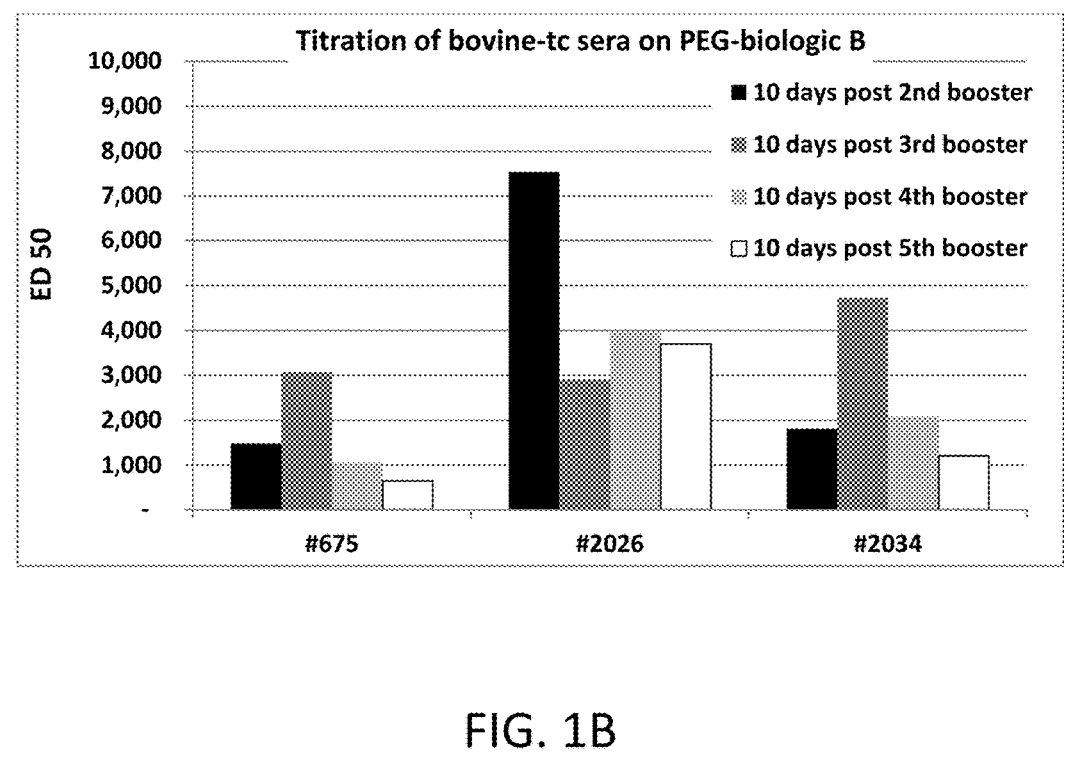

FIG. 1A and FIG. 1B show titrations of immunized bovine-tc sera against two PEGylated therapeutic compounds demonstrating PEG-specific reactivity. Serum samples from human IgG transchromosmal bovines immunized with a PEG-KLH conjugate were collected after every booster and serially diluted in an ELISA on plates coated with a PEGylated therapeutic compound. ED50 values representing the reciprocal of serum dilution with 50% of its maximal binding are compared across three bovines. All pre-dose samples were <100. See Example 1.

DETAILED DESCRIPTION

Figure 1A:
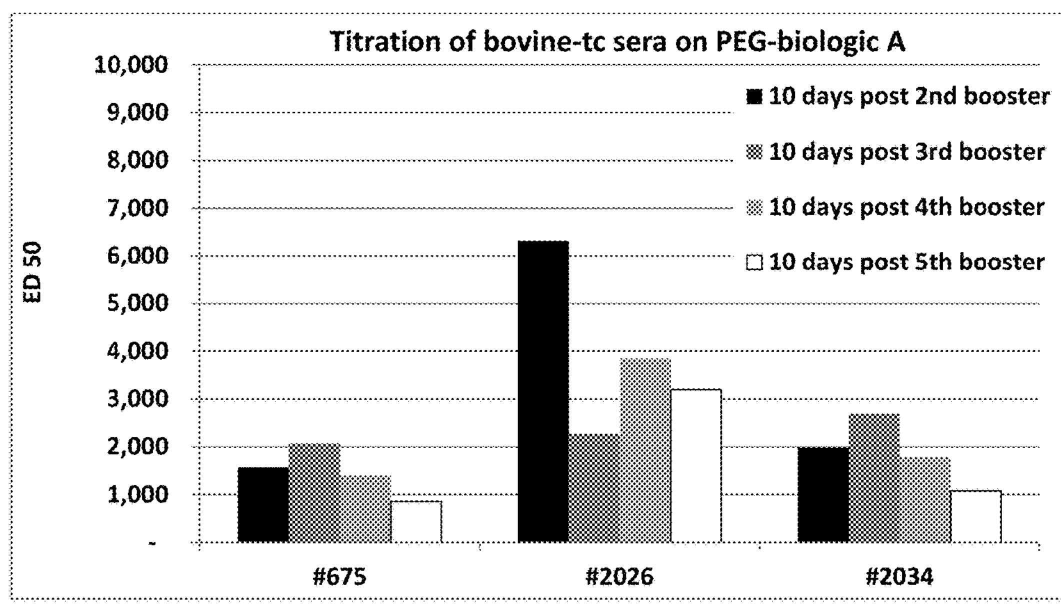

Polyethylene glycol (PEG) is a chemically inert polymer comprised of repeating units of ethylene oxide, either linear or branched, that ends with a methyl cap (mCap) and is conjugated with therapeutic proteins to enhance their PK properties. PEG is also variably present in food and cosmetics. Exposure to PEG may elicit antibodies specific to the backbone or to the methyl cap. Monitoring anti-PEG antibodies in human subjects who are dosed with PEGylated therapeutics may be required as part of immunogenicity assessment. The lack of well characterized anti-PEG reagents representing different isotypes, affinities and specificities to PEG have limited a thorough understanding of in vivo anti-PEG humoral response. We describe in detail the binding characteristics of a novel monoclonal and polyclonal human IgG Fc-bearing anti-PEG antibodies.

Polyclonal and monoclonal antibodies engineered with a human IgG1 Fc and reactive to PEG were developed to complement commercial anti-PEG antibodies. PEG with MW ranging from 350 daltons (Da) to 40 kilodaltons (kDa) were used to show that these antibodies had a MW-dependent binding. This was confirmed through the use of both surface plasmon resonance (SPR) based methods on BIACORE® and plate-based methods of direct binding to immobilized PEG as well as a homogenous assay in solution. Furthermore, specificity experiments using mCap mimicking analogs or PEG backbone structures with blocked mCaps revealed the specificity of these antibodies.

Affinity, specificity and MW of PEG are critical characteristics that impact interactions of custom generated anti-PEG antibodies with PEG. These results underscore the heterogeneity of anti-PEG antibodies and the limitations imposed by the MW of PEG molecule and the assay format on the ability to detect a broad diversity of anti-PEG antibodies formed as a result of exposure to a therapeutic or present pre-existing in human serum.

This application describes generation, purification and characterization of anti-PEG antibodies that might be suitable for an assay to detect anti-PEG antibodies in human subjects. Anti-PEG polyclonal and monoclonal antibodies engineered with a human Fc were generated for potential use in a direct assay format. To enable generic applications with these antibodies for multiple PEGylated therapeutics programs, biotin-conjugated PEG of varying molecular weights (MW) was used to characterize their binding to PEG using surface plasmon resonance (SPR) based methods on Biacore, and MSD (MesoScale Discovery) ECL (electrochemiluminescence)-based methods of direct binding to immobilized PEG as well as homogenous binding to PEG in solution. Since PEG is much smaller in MW in commercial cosmetic products and food additives than in therapeutics, pre-existing and therapeutic induced antibodies might be different. We therefore asked if MW of PEG had a bearing on backbone specific antibody binding. Our studies using PEG with molecular weights ranging from 350 daltons (Da) to 40 kDa demonstrates the influence of epitope density of —$(CH_2CH_2O)_n$ per strand on the binding of these antibodies. Competition assays using methyl cap (mCap) mimicking analogs or PEG backbone structures with blocked mCaps on either ends were used to identify the specificity of these antibodies.

Our work shows the complexity of these anti-PEG antibodies in relationship to their affinity and avidity to the length of the PEG backbone and to the specific epitope these antibodies recognize. The results underscore the heterogeneity of anti-PEG antibodies even to the same backbone structure and the limitations imposed by the selections of the PEG molecule and the assay format on the ability to detect anti-PEG antibodies with wide ranging specificity and varying affinities. We conclude robust assays capable of detecting the multitude of possible anti-PEG antibodies in humans require a diverse and well characterized panel of reagents as described here. See also Krishna et al. (2015) *Bioanalysis* 7:1869, the disclosure of which is hereby incorporated by reference in its entirety.

Definitions

In order that the present description may be more readily understood, certain terms are first defined. Additional definitions are set forth throughout the detailed description.

The term "antibody" as used to herein may include whole antibodies and any antigen binding fragments (i.e., "antigen-binding portions") or single chains thereof. An "antibody" refers, in one embodiment, to a glycoprotein comprising at least two heavy (H) chains and two light (L) chains inter-connected by disulfide bonds, or an antigen binding fragment thereof. Each heavy chain is comprised of a heavy chain variable region (abbreviated herein as $V_H$) and a heavy chain constant region. In certain naturally occurring IgG, IgD and IgA antibodies, the heavy chain constant region is comprised of three domains, CH1, CH2 and CH3. In certain naturally occurring antibodies, each light chain is comprised of a light chain variable region (abbreviated herein as $V_L$) and a light chain constant region. The light chain constant region is comprised of one domain, CL. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four framework regions (FRs), arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

An immunoglobulin may be from any of the commonly known isotypes, including but not limited to IgA, secretory IgA, IgG and IgM. The IgG isotype is divided in subclasses in certain species: IgG1, IgG2, IgG3 and IgG4 in humans, and IgG1, IgG2a, IgG2b and IgG3 in mice. Immunoglobulins, e.g., human IgG1, exist in several allotypes, which differ from each other in at most a few amino acids. "Antibody" may include, by way of example, monoclonal and polyclonal antibodies; chimeric and humanized antibodies; human and nonhuman antibodies; wholly synthetic antibodies; and single chain antibodies.

The term "antigen-binding portion" or "antigen binding fragment" of an antibody, as used herein, refers to one or more fragments of an antibody that retain the ability to specifically bind to an antigen (e.g., PEG).

Unless otherwise indicated, the word "fragment" when used with reference to an antibody, such as in a claim, refers to an antigen binding fragment of the antibody, such that "antibody or fragment" has the same meaning as "antibody or antigen binding fragment thereof."

The term "monoclonal antibody," as used herein, refers to an antibody that displays a single binding specificity and affinity for a particular epitope or a composition of antibodies in which all antibodies display a single binding specificity and affinity for a particular epitope. Typically such monoclonal antibodies will be derived from a single cell or nucleic acid encoding the antibody, and will be propagated without intentionally introducing any sequence alterations. Accordingly, the term "human monoclonal antibody" refers to a monoclonal antibody that has variable and optional constant regions derived from human germline immunoglobulin sequences. In one embodiment, human monoclonal antibodies are produced by a hybridoma, for example, obtained by fusing a B cell obtained from a transgenic or transchromosomal non-human animal (e.g., a transgenic mouse having a genome comprising a human heavy chain transgene and a light chain transgene), to an immortalized cell. Notwithstanding, as used herein, the term "monoclonal antibody" includes antibody PEG.1, which has two distinct light chains even if it would not typically be considered "monoclonal." Unless otherwise indicated, PEG.1 includes antibodies comprising exclusively light chain a or exclusively light chain b, or a mixture of antibody species with both light chains.

The term "recombinant human antibody," as used herein, includes all human antibodies that are prepared, expressed, created or isolated by recombinant means, such as (a) antibodies isolated from an animal (e.g., a mouse or cow) that is transgenic or transchromosomal for human immunoglobulin genes or a hybridoma prepared therefrom, (b) antibodies isolated from a host cell transformed to express the antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies comprise variable and constant regions that use particular human germline immunoglobulin sequences are encoded by the germline genes, but include subsequent rearrangements and mutations that occur, for example, during antibody maturation. As known in the art (see, e.g., Lonberg (2005) Nature Biotech. 23(9): 1117-1125), the variable region contains the antigen binding domain, which is encoded by various genes that rearrange to form an antibody specific for a foreign antigen. In addition to rearrangement, the variable region can be further modified by multiple single amino acid changes (referred to as somatic mutation or hypermutation) to increase the affinity of the antibody to the foreign antigen. The constant region will change in further response to an antigen (i.e., isotype switch). Therefore, the rearranged and somatically mutated nucleic acid sequences that encode the light chain and heavy chain immunoglobulin polypeptides in response to an antigen may not be identical to the original germline sequences, but instead will be substantially identical or similar (i.e., have at least 80% identity).

A "human" antibody refers to an antibody having variable regions in which both the framework and CDR regions are derived from human germline immunoglobulin sequences. Furthermore, if the antibody contains a constant region, the constant region also is derived from human germline immunoglobulin sequences. The antibodies described herein may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences. The terms "human" antibodies and "fully human" antibodies are used synonymously.

However, previous definitions notwithstanding, when referring to the polyclonal antibodies disclosed herein (e.g. #2026) derived from transgenic cows, "human" antibodies refers to antibodies comprising heavy chains derived exclusively from human germline immunoglobulin sequences. These antibodies may comprise light chains derived from human or bovine light chain germline sequences, likely with more bovine than human light chains, including antibodies with both human and bovine light chains.

A "chimeric antibody" refers to an antibody in which the variable regions are derived from one species and the constant regions are derived from another species, such as an antibody in which the variable regions are derived from a mouse antibody and the constant regions are derived from a human antibody.

As used herein, "isotype" refers to the antibody class (e.g., IgG1, IgG2, IgG3, IgG4, IgM, IgA1, IgA2, IgD, and IgE antibody) that is encoded by the heavy chain constant region genes.

"Allotype" refers to naturally occurring variants within a specific isotype group, which variants differ in a few amino acids (see, e.g., Jefferis et al. (2009) *mAbs* 1:1).

The phrases "an antibody recognizing an antigen" and "an antibody specific for an antigen" are used interchangeably herein with the term "an antibody which binds specifically to an antigen."

An "isolated antibody," as used herein, is intended to refer to an antibody that is substantially free of other antibodies having different antigenic specificities.

An "Fc region" (fragment crystallizable region) or "Fc domain" or "Fc" refers to the C-terminal region of the heavy chain of an antibody that mediates the binding of the immunoglobulin to host tissues or factors, including binding to Fc receptors located on various cells of the immune system (e.g., effector cells) or to the first component (C1q) of the classical complement system. Thus, an Fc region comprises the constant region of an antibody excluding the first constant region immunoglobulin domain (e.g., CH1 or CL). In IgG, IgA and IgD antibody isotypes, the Fc region comprises $C_{H2}$ and $C_{H3}$ constant domains in each of the antibody's two heavy chains; IgM and IgE Fc regions comprise three heavy chain constant domains ($C_H$ domains 2-4) in each polypeptide chain. For IgG, the Fc region comprises immunoglobulin domains Cγ2 and Cγ3 and the hinge between Cγ1 and Cγ2. Although the boundaries of the Fc region of an immunoglobulin heavy chain might vary, the human IgG heavy chain Fc region is usually defined to stretch from an amino acid residue at position C226 or P230 (or amino acid between these two amino acids) to the carboxy-terminus of the heavy chain, wherein the numbering is according to the EU index as in Kabat. Kabat et al. (1991) *Sequences of Proteins of Immunological Interest*, National Institutes of Health, Bethesda, Md.; see also FIGS. 3c-3f of U.S. Pat. App. Pub. No. 2008/0248028. The $C_{H2}$ domain of a human IgG Fe region extends from about amino acid 231 to about amino acid 340, whereas the $C_{H3}$ domain is positioned on C-terminal side of a $C_{H2}$ domain in an Fc region, i.e., it extends from about amino acid 341 to about amino acid 447 of an IgG. As used herein, the Fc region may be a native sequence Fc, including any allotypic variant, or a variant Fc (e.g., a non-naturally occurring Fc). Fc may also refer to this region in isolation or in the context of an Fc-comprising protein polypeptide such as a "binding protein comprising an Fc region," also referred to as an "Fc fusion protein" (e.g., an antibody or immunoadhesin).

A "native sequence Fc region" or "native sequence Fc" comprises an amino acid sequence that is identical to the amino acid sequence of an Fc region found in nature. Native sequence human Fc regions include a native sequence human IgG1 Fc region; native sequence human IgG2 Fc region; native sequence human IgG3 Fc region; and native sequence human IgG4 Fc region as well as naturally occurring variants thereof. Native sequence Fc include the various allotypes of Fcs. See, e.g., Jefferis et al. (2009) *mAbs* 1:1.

The term "epitope" or "antigenic determinant" refers to a site on an antigen (e.g., PEG) to which an immunoglobulin or antibody specifically binds. Epitopes within polymer antigens can be formed both from contiguous residues or noncontiguous residues juxtaposed by tertiary folding of the polymer.

Antibodies that "compete with another antibody for binding to a target" refer to antibodies that inhibit (partially or completely) the binding of the other antibody to the target. Whether two antibodies compete with each other for binding to a target, i.e., whether and to what extent one antibody inhibits the binding of the other antibody to a target, may be determined using known competition experiments. In certain embodiments, an antibody competes with, and inhibits binding of another antibody to a target by at least 10%, 20%, 30%, 40%, 50%, 60%, 70%, 80%, 90% or 100%. The level of inhibition or competition may be different depending on which antibody is the "blocking antibody" (i.e., the cold antibody that is incubated first with the target). Competition assays can be conducted as described, for example, in Ed Harlow and David Lane, Cold Spring Harb. Protoc.; 2006; doi:10.1101/pdb.prot4277 or in Chapter 11 of "Using Antibodies" by Ed Harlow and David Lane, Cold Spring Harbor Laboratory Press, Cold Spring Harbor, N.Y., USA 1999. Competing antibodies bind to the same epitope, an overlapping epitope or to adjacent epitopes (e.g., as evidenced by steric hindrance).

Other competitive binding assays include: solid phase direct or indirect radioimmunoassay (RIA), solid phase direct or indirect enzyme immunoassay (EIA), sandwich competition assay (see Stahli et al. (1983) *Methods in Enzymology* 9:242); solid phase direct biotin-avidin EIA (see Kirkland et al. (1986) *J Immunol.* 137:3614); solid phase direct labeled assay, solid phase direct labeled sandwich assay (see Harlow and Lane (1988), *Antibodies: A Laboratory Manual*, Cold Spring Harbor Press); solid phase direct label MA using 1-125 label (see Morel et al. (1988) *Mol. Immunol.* 25(1):7); solid phase direct biotin-avidin EIA (Cheung et al. (1990) *Virology* 176:546); and direct labeled MA. (Moldenhauer et al. (1990) *Scand. J. Immunol.* 32:77).

As used herein, the terms "specific binding," "selective binding," "selectively binds," and "specifically binds," refer to antibody binding to an epitope on a predetermined antigen but not to other antigens.

Also provided are "conservative sequence modifications" to the antibody sequence provided herein, i.e. nucleotide and amino acid sequence modifications that do not abrogate the binding of the antibody encoded by the nucleotide sequence or containing the amino acid sequence, to the antigen. For example, modifications can be introduced by standard techniques known in the art, such as site-directed mutagenesis and PCR-mediated mutagenesis. Conservative sequence modifications include conservative amino acid substitutions, in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, a predicted nonessential amino acid residue in an anti-PEG antibody is preferably replaced with another amino acid residue from the same side chain family. Methods of identifying nucleotide and amino acid conservative substitutions that do not eliminate antigen binding are well-known in the art. See, e.g., Brummell et al., *Biochem.* 32:1180-1187 (1993); Kobayashi et al. *Protein Eng.* 12(10):879-884 (1999); and Burks et al. *Proc. Natl. Acad. Sci. USA* 94:412-417 (1997).

For nucleic acids, the term "substantial homology" indicates that two nucleic acids, or designated sequences thereof, when optimally aligned and compared, are identical, with appropriate nucleotide insertions or deletions, in at least about 80% of the nucleotides, usually at least about 90% to 95%, and more preferably at least about 98% to 99.5% of the nucleotides. Alternatively, substantial homology exists when the segments will hybridize under selective hybridization conditions, to the complement of the strand.

For polypeptides, the term "substantial homology" indicates that two polypeptides, or designated sequences thereof, when optimally aligned and compared, are identical, with appropriate amino acid insertions or deletions, in at least about 80% of the amino acids, usually at least about 90% to 95%, and more preferably at least about 98% to 99.5% of the amino acids.

The percent identity between two sequences is a function of the number of identical positions shared by the sequences when the sequences are optimally aligned (i.e., % homology=# of identical positions/total # of positions×100), with optimal alignment determined taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two nucleotide sequences can be determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (CABIOS, 4:11-17 (1989)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* (48):444-453 (1970)) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6.

As used herein, the term "linked" refers to the association of two or more molecules. The linkage can be covalent or non-covalent. The linkage also can be genetic (i.e., recombinantly fused). Such linkages can be achieved using a wide variety of art recognized techniques, such as chemical conjugation and recombinant protein production.

As used herein, a standard curve for an assay may comprise one or more data points obtained using one or more standard ("control") samples of known concentration of analyte (or analyte surrogate). In various embodiments, the human IgG anti-PEG antibodies of the present invention serve as surrogates for human IgG anti-PEG antibodies that are present in samples from human subjects. The signal (read-out) from the assay is determined for the one or more control determinations and used to infer the concentration of analyte in experimental (non-control) samples, e.g. the titer of anti-drug antibodies. As used herein, a standard curve includes even a single concentration, despite any definitions to the contrary, which may be useful in qualitative verification of an assay and confirmation of consistent output signal between experiments.

Unless otherwise indicated or clear from the context, PEG refers to polyethylene glycol of any molecular weight.

PEG. 2 and PEG.1 refer to chimeric monoclonal anti-PEG antibodies as disclosed herein, comprising mouse variable domains and human constant domains. PEG.1 has two distinct light chain sequences, SEQ ID NOs: 8 and 10, referred to herein as PEG.1a and PEG.1b, respectively. See Table 3.

A "human subject," as used herein, refers generally to humans without regard to disease status, treatment status or diagnosis. A human subject may be diagnosed with a disorder necessitating treatment with a PEGylated therapeutic compound, but need not be diagnosed. A human subject may or may not have been previously treated, e.g. with a PEGylated therapeutic compound.

As used herein, "qualitative" determination of anti-PEG antibodies refers to a determination sufficient to confirm the presence or absence of the antibodies but not a specific titer. "Semi-quantitative" determination of the level of anti-PEG antibodies provides a numerical value for the titer sufficient to guide treatment decisions.

As used herein, a "bridging assay," when used with reference to detection of anti-PEG antibodies, is an assay where a positive signal arises from binding of two different PEGylated drug molecules to a single anti-PEG antibody (IgG or IgM) to form a drug1-anti-PEG-drug2 ternary complex. A detectable signal arises from the formation of this ternary complex. In some embodiments, drug1 is bound to a surface and drug2 is only tethered to that surface if there is a bivalent binding reagent (e.g. anti-PEG antibody) present in the sample. In other embodiments the proximity of drug1 and drug2 when bound to the same anti-PEG antibody allows for energy transfer, giving rise to a detectable signal. A "direct assay," in contrast, typically involves binding of the anti-PEG antibody to PEG bound to a surface, and subsequent direct detection of the anti-PEG antibody, e.g. by a reagent that binds to the Fc portion of the anti-PEG antibodies.

"Sample," as used herein with reference to samples for detecting anti-PEG antibodies, refers to any type of sample suitable for such detection, including but not limited to blood, serum or any other blood fraction in which such antibodies may be detected. A sample may obtained as whole blood but used in an assay as serum, for example, but both would be considered "samples" for purposes of the present invention.

Various aspects described herein are described in further detail in the following subsections.

Anti-PEG Antibodies

PEGylation of biotherapeutics is a commonly used approach in Biotechnology to improve pharmacological bioavailability of biotherapeutic products. Kang et al. (2009) *Expert Opin. Emerg. Drugs* 14:363; Fishburn et al. (2008) 1 *Pharm. Sci.* 97:4167. Most therapeutic molecules tend to have PEG conjugates with sizes exceeding 10-20 kD in MW. Investigations on the immunogenicity of biotherapeutics have brought the role of PEG in focus. While commercial anti-PEG IgM antibodies have been used for ADA assay development, there are no well characterized reagents nor robust methods available to confirm or refute presence and kinetics of an anti-PEG IgG response. Making interpretation of any such assay is rendered more complex by the presence of endogenously occurring anti-PEG antibodies that are elicited in response to exposure to ubiquitously present PEG in many commercial products as well as in food. Garay et al. (2012) *Expert Opin. Drug Deliv.* 9:1319. It is unclear whether such pre-existing antibodies play any role in an immune response to the PEG portion of a biotherapeutic and if there are any downstream consequences on safety and efficacy. Schellekens et al. (2013) *Pharm. Res.* 30:1729. Underlying these issues has been a lack of well characterized and understood reagents and methods to accurately and reproducibly detect anti-PEG IgG in human clinical samples.

The generation and purification of anti-PEG IgG pAb were quite different from similar processes to raise pAbs to protein or peptide immunogens. Their binding affinity to PEG is relatively weak and necessitates the use of several booster doses, stronger adjuvants and the use of stoichiometric excess of PEG on KLH conjugates to elicit strong reactive anti-PEG antibody titer. We believe the higher signal intensity from the polyclonal bovine antibody could be accounted to the high dose of KLH conjugated PEG and the high molar ratio of PEG in the conjugate used in immunizations; in contrast the monoclonal PEG.2 clone was identified from mice immunized with a mixture PEGylated therapeutic molecules. However, given the unusual genetic background of the human IgG-expressing transchromosomal bovine models, this may need to be confirmed in other larger mammals typically used to raise polyclonal antibodies.

Several groups that have raised antibodies to PEG in rabbits have reported the immunogenic importance of the methoxy group in eliciting anti-PEG antibodies. Sherman et al. (2012) *Bioconjug. Chem.* 23(3):485; Saifer et al. (2014) *Mol. Immunol.* 57:236. The polyclonal antibodies from the bovines used in this study did not appear to have a preferential reactivity to the methoxy group; our specificity data suggests strong backbone specificity. Saifer et al. (2014 *Mol. Immunol.* 57:236) reported several factors including the backbone length influencing the selectivity of their anti-PEG antibodies; our data is in alignment with the reported effect of PEG MW on antibody binding. Furthermore in contrast to standard anti-protein polyclonal antibody purification processes anti-PEG polyclonal antibody involved batch purification steps and repeated re-runs of the flow-through material over the PEG affinity column; these antibodies tends to form fairly significant amount of aggregation post elution from affinity column and will require additional preparative SEC steps for isolation of the monomeric IgG species. Aggregation affected buffer stability at cold as well as enhanced freeze thaw instability. Use of TWEEN®-based detergents significantly impacted our assays due to their cross reactivity with the PEG backbone and relates to such observations from other groups. Saifer et al. (2014) *Mol. Immunol.* 57:236.

Recognition of PEG by Anti-PEG Antibody is Influenced by the Size of the PEG Molecule Our current understanding of the immunogenic domains in a PEG molecule has probably oversimplified the role of the chain length in recognition to backbone subunits. There are perhaps other secondary structural constraints native to the full length of the PEG molecule that influences recognition of different antibodies binding to the same subunit in the context of PEG MW. While the monoclonal PEG.2 clearly preferred the larger size PEG and was unable to recognize the same subunits on a smaller version of the PEG, the polyclonal did not exhibit such bias. These antibodies show markedly different binding and specificity profiles to PEG independent of the platform and assay structure implying that the selection of PEG in an assay can clearly influence its ability to detect anti-PEG antibodies. Moreover differences between the direct and semi-homogeneous formats show the advantage of using direct binding assays to obtain stronger signals; directly immobilized PEG was a better way to capture anti-PEG antibodies than PEG used in solution. This is in contrast to most conventional immunogenicity assays where labeled therapeutic molecules are used in solution to detect ADAs recognizing epitopes on a protein structure of the therapeutic.

While it would be prudent to use a similar size PEG as used in the therapeutic to detect any induced antibodies, alternate low MW forms might be needed for detection of pre-existing antibodies that are believed to be triggered by low MW PEG products in naturally occurring products. A heterogeneous mixture of PEG molecules of varying lengths can be used in assays to pick up a far more diverse range of anti-PEG antibodies. Most antibodies probably have some degree of reactivity to the backbone subunit; even the commercial rabbit antibody B-47 believed to be methyl cap specific showed some dependence on subunits. Our results underscore the heterogeneity of anti-PEG antibodies and the limitations imposed by the selections of the PEG molecule and the assay format on the ability to detect all species of anti-PEG antibodies formed as a result of exposure to a therapeutic or pre-existing in human serum. In order to develop robust assays capable of detecting the multitude of possible anti-PEG antibodies in humans, the reagents used to develop any anti-PEG antibody immunogenicity assay will need to be thoroughly characterized in terms of their specificity, dependence on MW of PEG and their affinity before any subject data can be meaningfully interpreted. O'Hara et al. (2012) *AAPS J.* 14:316.

Implications

Many PEGylated products have been approved by Health authorities. Over time there has been little evidence of a sustained anti-PEG immunogenic response with any link to the product's efficacy or safety. This might be related to the lack of robust and reliable methods and reagents to demonstrate evidence (or lack thereof) of anti-PEG immunogenicity. PEG tends to be immunologically inert and is widely believed to elicit low affinity antibodies, typically IgM; Based on our experience, we assume the inherent difficulties in generating and purifying polyclonal anti-PEG IgG might have constrained reagent availability and impeded the development of methods to detect IgG anti-PEG antibodies Unlike immunogenic responses to proteins that can be driven to affinity maturation following chronic exposure, the immunogenicity to PEG could span a wide spectrum ranging from low affinity interactions to moderately high. Pre-existing antibodies that arise following long term exposure to PEG in nutritional and cosmetic products may also influence maturation of IgG antibodies. The present classification of anti-PEG antibodies as being either anti-backbone or anti-methyl cap or anti-linker does not fully represent their wide diversity. The MW or length and branching structure of the PEG used in any assay to identify anti-PEG antibodies could skew their detection. The analytical challenge is to develop assays designed to detect IgG response to PEG and reflecting the innate diversity of anti-PEG antibodies in human subjects—capable of picking low affinity antibodies, the pre-existing antibodies following a boost in their titer, and the induced antibodies elicited by the PEG conjugate specific to the therapeutic product and antibodies that might differentially bind to the backbone subunit based on shape, length of the PEG and the assay format. The different IgG responses are likely to have very different analytical outcomes in any one assay. Unlike the conventional approaches to developing materials and methods for a typical anti-protein therapeutic IgG assay the PEG poses new questions and compels us to think about a need for wider array of well characterized reagents whose analytical behavior in an immunogenicity assay should be reflecting those found in the human subjects. Since PEG is a commonly used adduct with several therapeutic molecules, the methods and reagents should be ideally made available for standardization across different PEGylated platforms amenable for comparative and cooperative research to confidently rule in or out the role of PEG in immune mediated aberrations on the pharmacological activity of the therapeutic.

Anti-PEG Antibodies that Compete with Anti-PEG Antibodies Disclosed Herein

Anti-PEG antibodies that compete with the antibodies of the present invention for binding to PEG, such as PEG.2 (clone 6A9) or PEG.1 (clone 14B5), may be raised using immunization protocols similar to those described herein.

Competing antibodies can be identified using methods known in the art. For example, standard ELISA assays or competitive ELISA assays can be used in which PEG is immobilized on the plate, various concentrations of unlabeled first antibody are added, the plate is washed, labeled second antibody is added, washed, and the amount of bound label is measured. If the increasing concentration of the unlabeled (first) antibody (also referred to as the "blocking antibody") inhibits the binding of the labeled (second) antibody, the first antibody is said to inhibit the binding of the second antibody to the target on the plate, or is said to compete with the binding of the second antibody. Additionally or alternatively, BIACORE® SPR analysis can be used to assess the ability of the antibodies to compete. The ability of a test antibody to inhibit the binding of an anti-PEG antibody described herein to PEG demonstrates that the test antibody can compete with the antibody for binding to PEG.

Accordingly, provided herein are anti-PEG antibodies that inhibit the binding of an anti-PEG antibody described herein to PEG by at least 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100% and/or whose binding to PEG is inhibited by at least 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100%, e.g., as measured by ELISA.

Anti-PEG Antibody Sequence Variants

Some variability in the antibody sequences disclosed herein may be tolerated and still maintain the desirable properties of the antibody. The CDR regions are delineated using the Kabat system (Kabat, E. A., et al. (1991) Sequences of Proteins of Immunological Interest, Fifth Edition, U.S. Department of Health and Human Services, NIH Publication No. 91-3242). Accordingly, the present invention further provides anti-PEG antibodies comprising CDR sequences that are at least 70%, 75%, 80%, 85%, 90%, 95%, 96%, 97%, 98%, or 99% identical to the CDR sequences of the antibodies disclosed herein (e.g. PEG.1 and PEG.2). The present invention also provides anti-PEG antibodies comprising heavy and/or light chain variable domain sequences that are at least 70%, 75%, 80%, 85%, 90%, 95%, 96%, 97%, 98%, or 99% identical to the heavy and/or light chain variable domain sequences of the antibodies disclosed herein (e.g. PEG.1 and PEG.2).

Fcs and Modified Fcs

Accordingly, anti-PEG variable regions described herein may be linked (e.g., covalently linked or fused) to an Fc, e.g., an IgG1, IgG2, IgG3 or IgG4 Fc, which may be of any allotype or isoallotype, e.g., for IgG1: G1m, G1m1(a), G1m2(x), G1m3(f), G1m17(z); for IgG2: G2m, G2m23(n); for IgG3: G3m, G3m21(g1), G3m28(g5), G3m11(b0), G3m5(b1), G3m13(b3), G3m14(b4), G3m10(b5), G3m15(s), G3m16(t), G3m6(c3), G3m24(c5), G3m26(u), G3m27(v). See, e.g., Jefferis et al. (2009) mAbs 1:1).

Labeled Anti-PEG Antibodies

Anti-PEG antibodies of the present invention may be labeled with detectable labels. Such labeled antibodies may find use, e.g., in ELISAs, fluorescence-activated cell sorting (FACS), immunohistochemistry (IHC) or any other application for detection of PEG or PEGylated compounds. Any suitable label may be used, including, but are not limited to, 5-(and 6)-carboxyfluorescein, 5- or 6-carboxyfluorescein, 6-(fluorescein)-5-(and 6)-carboxamido hexanoic acid, fluorescein isothiocyanate, rhodamine, tetramethylrhodamine, Cy2, Cy3, Cy5, AMCA, PerCP, R-phycoerythrin (RPE), allophycoerythrin (APC), Texas Red, Princeton Red, Green fluorescent protein (GFP), coated CdSe nanocrystallites, DNP, biotin, digoxiginin, horseradish peroxidase (HRP), alkaline phosphatase (AP), beta-galactosidase (GAL), glucose-6-phosphate dehydrogenase, β-N-acetylglucosaminidase, β-glucuronidase, invertase, Xanthine Oxidase, firefly luciferase, glucose oxidase (GO), luminol, isoluminol, acridinium esters, 1,2-dioxetanes, 1,2-pyridopyridazines, or radioactive isotopes of hydrogen, carbon, sulfur, iodide, cobalt, selenium, tritium, or phosphorous.

Additional Uses

As described herein, the anti-PEG antibodies of the present invention are uniquely useful in development and validation of assays for detection of anti-drug antibodies against PEGylated therapeutic compounds, e.g. for use as positive control samples for direct binding assays for detection of human IgG anti-PEG antibodies using PEG capture. In addition to such screening, the anti-PEG antibodies of the present invention may find use in any context where it would be useful to selectively bind or detect PEG or PEGylated compounds. For example, the antibodies may also be used in confirmatory assays in which free PEG is added to confirm that observed binding in an assay is PEG-specific. The antibodies may also find use in assays in which acid dissociation is used to disrupt complexes of anti-PEG antibodies and a PEGylated therapeutic compound that might otherwise interfere with anti-PEG antibody detection.

Nucleic Acid Molecules

Another aspect described herein pertains to nucleic acid molecules that encode the antibodies described herein. The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids (e.g., other chromosomal DNA, e.g., the chromosomal DNA that is linked to the isolated DNA in nature) or proteins, by standard techniques, including alkaline/SDS treatment, CsCl banding, column chromatography, restriction enzymes, agarose gel electrophoresis and others well known in the art. See, F. Ausubel, et al., ed. (1987) Current Protocols in Molecular Biology, Greene Publishing and Wiley Interscience, New York. A nucleic acid described herein can be, for example, DNA or RNA and may or may not contain intronic sequences. In a certain embodiments, the nucleic acid is a cDNA molecule.

Nucleic acids described herein can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), nucleic acid encoding the antibody can be recovered from the library.

Once DNA fragments encoding VH and VL segments are obtained, these DNA fragments can be further manipulated by standard recombinant DNA techniques, for example to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the VH region can be converted to a full-length heavy chain gene by operatively linking the VH-encoding DNA to another DNA molecule encoding heavy chain constant regions (hinge, CH1, CH2 and/or CH3). The sequences of human heavy chain constant region genes are known in the art (see e.g., Kabat, E. A., el al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region, for example, an IgG1 region. For a Fab fragment heavy chain gene, the VH-encoding DNA can be operatively linked to another DNA molecule encoding only the heavy chain CH1 constant region.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or lambda constant region.

Antibody Manufacture: Generation of Transfectomas Producing Monoclonal Antibodies to PEG Antibodies of the present invention, including both specific antibodies for which sequences are provided and other, related anti-PEG antibodies, can be produced in a host cell transfectoma using, for example, a combination of recombinant DNA techniques and gene transfection methods as is well known in the art. Morrison, S. (1985) *Science* 229: 1202.

For example, to express antibodies, or antibody fragments thereof, DNAs encoding partial or full-length light and heavy chains, can be obtained by standard molecular biology techniques (e.g., PCR amplification or cDNA cloning using a hybridoma that expresses the antibody of interest) and the DNAs can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or both genes are inserted into the same expression vector. The antibody genes are inserted into the expression vector(s) by standard methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the $V_H$ segment is operatively linked to the $C_H$ segment(s) within the vector and the $V_L$ segment is operatively linked to the $C_L$ segment within the vector.

Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, recombinant expression vectors may carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel (Gene Expression Technology. Methods in Enzymology 185, Academic Press, San Diego, Calif. (1990)). It will be appreciated by those skilled in the art that the design of the expression vector, including the selection of regulatory sequences, may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP) and polyoma. Alternatively, non-viral regulatory sequences may be used, such as the ubiquitin promoter or β-globin promoter. Still further, regulatory elements composed of sequences from different sources, such as the SRα promoter system, which contains sequences from the SV40 early promoter and the long terminal repeat of human T cell leukemia virus type 1. Takebe et al. (1988) *Mol. Cell. Biol.* 8:466-472.

In addition to the antibody chain genes and regulatory sequences, recombinant expression vectors may carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies described herein in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss, M. A. and Wood, C. R. (1985) Immunology Today 6:12-13). Antibodies of the present invention can also be produced in glycoengineered strains of the yeast *Pichia pastoris*. Li et al. (2006) *Nat. Biotechnol.* 24:210.

Preferred mammalian host cells for expressing the recombinant antibodies described herein include Chinese Hamster Ovary (CHO cells) (including dhfr-CHO cells, described in Urlaub and Chasin, (1980) Proc. Natl. Acad. Sci. USA 77:4216-4220, used with a DHFR selectable marker, e.g., as described in R. J. Kaufman and P. A. Sharp (1982) Mol. Biol. 159:601-621), NSO myeloma cells, COS cells and SP2 cells. In particular, for use with NSO myeloma cells, another preferred expression system is the GS gene expression system disclosed in WO 87/04462, WO 89/01036 and EP 338,841. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

The N- and C-termini of antibody polypeptide chains of the present invention may differ from the expected sequence due to commonly observed post-translational modifications. For example, C-terminal lysine residues are often missing from antibody heavy chains. Dick et al. (2008) *Biotechnol. Bioeng.* 100:1132. N-terminal glutamine residues, and to a lesser extent glutamate residues, are frequently converted to pyroglutamate residues on both light and heavy chains of therapeutic antibodies. Dick et al. (2007) *Biotechnol. Bioeng.* 97:544; Liu et al. (2011) *JBC* 28611211; Liu et al. (2011) *J. Biol. Chem.* 286:11211.

The present invention comprises numerous embodiments. Various exemplary embodiments are provided at Table 1.

TABLE 1

| Embodiments |
|---|
| 1. An isolated chimeric anti-PEG antibody, or PEG-binding fragment thereof, comprising:<br>a. a non-human variable domain; and<br>b. a human IgG constant domain. |
| 2. An isolated anti-PEG antibody that competes with antibody PEG.2 or PEG.1 for binding to PEG; wherein<br>a. antibody PEG.2 comprises:<br>i. the heavy chain variable domain sequence of SEQ ID NO: 2; and<br>ii. the light chain variable domain sequence of SEQ ID NO: 4; and<br>b. antibody PEG.1 comprises:<br>i. the heavy chain variable domain sequence of SEQ ID NO: 6; and<br>ii. the light chain variable domain sequence of SEQ ID NO: 8 or SEQ ID NO: 10. |
| 3. The isolated anti-PEG antibody of Embodiment 2 wherein<br>a. antibody PEG.2 comprises:<br>i. the heavy chain sequence of SEQ ID NO: 11; and<br>ii. the light chain sequence of SEQ ID NO: 12; and<br>b. antibody PEG.1 comprises:<br>i. the heavy chain sequence of SEQ ID NO: 13; and<br>ii. the light chain sequence of SEQ ID NO: 14. |
| 4. An isolated anti-PEG antibody comprising:<br>a. a heavy chain variable domain comprising:<br>i. CDRH1 (residues 31-35 of SEQ ID NO: 2);<br>ii. CDRH2 (residues 50-68 of SEQ ID NO: 2); and<br>iii. CDRH3 (residues 101-109 of SEQ ID NO: 2) of antibody PEG.2, or<br>i. CDRH1 (residues 31-35 of SEQ ID NO: 6);<br>ii. CDRH2 (residues 50-66 of SEQ ID NO: 6); and<br>iii. CDRH3 (residues 99-110 of SEQ ID NO: 6) of antibody PEG.1, and<br>b. a light chain variable domain comprising:<br>i. CDRL1 (residues 31-37 of SEQ ID NO: 4);<br>ii. CDRL2 (residues 50-56 of SEQ ID NO: 4); and<br>iii. CDRL3 (residues 89-102 of SEQ ID NO: 4) of antibody PEG.2, or<br>i. CDRL1 (residues 24-34 of SEQ ID NO: 8);<br>ii. CDRL2 (residues 50-56 of SEQ ID NO: 8); and<br>iii. CDRL3 (residues 89-102 of SEQ ID NO: 8) of antibody PEG.1a, or<br>i. CDRL1 (residues 24-39 of SEQ ID NO: 10);<br>ii. CDRL2 (residues 55-61 of SEQ ID NO: 10); and<br>iii. CDRL3 (residues 94-102 of SEQ ID NO: 10) of antibody PEG.1b. |

TABLE 1-continued

| Embodiments |
| --- |

5. The isolated anti-PEG antibody of Embodiment 4 comprising heavy and light chain variable domains with at least 95% sequence identity with the heavy and light chain variable domains of antibody PEG.2 or PEG.1; wherein
    a. antibody PEG.2 comprises:
        i. the heavy chain variable domain sequence of SEQ ID NO: 2; and
        ii. the light chain variable domain sequence of SEQ ID NO: 4;
        and
    b. antibody PEG.1 comprises:
        i. the heavy chain variable domain sequence of SEQ ID NO: 6; and
        ii. the light chain variable domain sequence of SEQ ID NO: 8 or SEQ ID NO: 10,
        wherein the antibody retains the ability to bind to PEG.
6. The isolated anti-PEG antibody of Embodiment 5 wherein the anti-PEG antibody comprises:
    a. the heavy chain variable domain sequence of SEQ ID NO: 2 and the light chain variable domain sequence of SEQ ID NO: 4; or
    b. the heavy chain variable domain sequence of SEQ ID NO: 6 and the light chain variable domain sequence of SEQ ID NO: 8 or SEQ ID NO: 10.
7. The isolated anti-PEG antibody of any of Embodiments 4, 5 and 6 further comprising a human IgG constant domain.
8. The isolated anti-PEG antibody of Embodiment 4 comprising heavy and light chains with at least 95% sequence identity with the heavy and light chains of antibody PEG.2 or PEG.1; wherein
    a. antibody PEG.2 comprises:
        i. the heavy chain sequence of SEQ ID NO: 11; and
        ii. the light chain sequence of SEQ ID NO: 12;
        and
    b. antibody PEG.1 comprises:
        i. the heavy chain sequence of SEQ ID NO: 13; and
        ii. the light chain sequence of SEQ ID NO: 14,
        wherein the antibody retains the ability to bind to PEG.
9. The isolated anti-PEG antibody of Embodiment 8 wherein the anti-PEG antibody comprises:
    a. the heavy chain sequence of SEQ ID NO: 11 and the light chain sequence of SEQ ID NO: 12; or
    b. the heavy chain sequence of SEQ ID NO: 13 and the light chain sequence of SEQ ID NO: 14.
10. The isolated anti-PEG antibody of Embodiment 9 wherein the anti-PEG antibody comprises the heavy chain sequence of SEQ ID NO: 11 and the light chain sequence of SEQ ID NO: 12.
11. The isolated anti-PEG antibody of Embodiment 9 wherein the anti-PEG antibody comprises the heavy chain sequence of SEQ ID NO: 13 and the light chain sequence of SEQ ID NO: 14.
12. An isolated anti-PEG antibody comprising:
    a. a murine heavy chain variable domain derived from heavy chain germline:
        i. V domain 3-11;
        ii. D domain 4-17; and
        iii. J domain JH4a or Jh4d;
        and
    b. a murine light chain variable domain derived from light chain germline:
        i. V domain A21 or A17; and
        ii. J domain JK1 or JK2.
13. An isolated human IgG anti-PEG antibody, or PEG-binding fragment thereof, isolated from a cow.
14. The isolated human IgG anti-PEG antibody or fragment of Embodiment 13 comprising human heavy chains and at least one bovine light chain.
15. An isolated polyclonal human IgG anti-PEG antibody, or PEG-binding fragment thereof, of Embodiment 13.
16. An isolated anti-PEG antibody that competes with polyclonal antibody #2026 for binding to PEG.
17. A method of validating an assay for human IgG anti-PEG antibodies in a sample from a human subject, comprising:
    a. exposing a PEG-coated surface to a sample from a human subject;
    b. washing the PEG-coated surface;
    c. detecting the presence or absence of human IgG anti-PEG antibodies bound to the PEG-coated surface, and
    d. performing a control experiment employing steps a, b, and c above except that a human IgG anti-PEG antibody of the present invention is substituted for the sample from a human subject, and/or is added to the sample from a human subject, at step a, such that the presence of human IgG anti-PEG antibodies of the present invention is observed at step c of the control experiment to validate that the assay is capable of detecting human IgG anti-PEG antibodies.
18. A method of creating a standard curve for an assay for human IgG anti-PEG antibodies in a sample from a human subject, comprising:
    a. exposing a PEG-coated surface to one or more samples containing a known concentration of at least one human Fc-containing anti-PEG antibody of the present invention;

TABLE 1-continued

| Embodiments |
| --- |
| b. washing the PEG-coated surface;<br>c. detecting the at least one human IgG anti-PEG antibody of the present invention bound to the PEG-coated surface,<br>wherein the signal detected for each known concentration is used to create a standard curve for determining the titer of human IgG anti-PEG antibodies in the sample from a human subject. |
| 19. The method of Embodiment 18 wherein only one sample containing a known concentration of at least one human IgG Fc-containing anti-PEG antibody of the present invention is used and the standard curve provides a qualitative answer regarding the presence or absence of human IgG anti-PEG antibodies in the sample from the human subject. |
| 20. The method of Embodiment 18 wherein more than one sample containing a known concentration of at least one human IgG Fc-containing anti-PEG antibody of the present invention is used and the standard curve provides a semi-quantitative value for the titer of human IgG anti-PEG antibodies in the sample from the human subject. |
| 21. A method of detecting human IgG anti-PEG antibodies in a sample from a human subject comprising:<br>a. exposing a PEG-coated surface to a sample from a human subject;<br>b. washing the PEG-coated surface;<br>c. detecting the presence or absence of human IgG anti-PEG antibodies bound to the PEG-coated surface; and<br>d. determining the presence, absence, or titer of human IgG anti-PEG antibodies in the sample from a human subject by comparing the results of step c with control experiments using one or more human IgG Fc-containing anti-PEG antibody of the present invention. |
| 22. A method of treating a human subject with a PEGylated therapeutic compound comprising:<br>a. obtaining a sample from the subject for use in an assay to detect the presence of human IgG anti-PEG antibodies;<br>b. detecting the presence, absence or titer of human IgG anti-PEG antibodies in the sample, wherein the presence, absence or titer of human IgG anti-PEG antibody in the sample is determined by comparing the results of this detection with a standard curve obtained using human IgG anti-PEG antibodies of the present invention as a positive control; and<br>c. modifying the treatment regimen with the PEGylated therapeutic compound as a consequence of the presence, absence or titer of human IgG anti-PEG antibodies in the sample. |
| 23. A method of treating a human subject with a PEGylated therapeutic compound comprising:<br>a. obtaining a sample from the subject for use in an assay to detect the presence of human IgG anti-PEG antibodies;<br>b. requesting that the titer of anti-PEG antibodies in the sample be determined, wherein the titer is determined with reference to a standard curve obtained using human IgG anti-PEG antibodies of the present invention as a positive control; and<br>c. modifying the treatment regimen with the PEGylated therapeutic compound as a consequence of the presence, absence or approximate titer of human IgG anti-PEG antibodies in the sample. |
| 24. The method of Embodiment 22 or 23 wherein the modifying at step c comprises reducing the dose of the PEGylated therapeutic compound or discontinuing therapy with the PEGylated therapeutic compound if the titer of human IgG anti-PEG antibodies in the sample is above a threshold level. |
| 25. The method of Embodiment 22 or 23 wherein the modifying at step c comprises treatment with one or more additional medicines to ameliorate unwanted side effects if the titer of human IgG anti-PEG antibodies in the sample is above a threshold level. |
| 26. A method of determining whether a human subject should be excluded from treatment with a PEGylated therapeutic compound comprising:<br>a. detecting the presence, absence or titer of human IgG anti-PEG antibodies in a sample obtained from the subject prior to treatment with the PEGylated therapeutic compound, wherein the titer is determined with reference to a standard curve obtained using human IgG anti-PEG antibodies of the present invention as a positive control; and<br>b. excluding the subject from treatment with the PEGylated therapeutic compound if human IgG anti-PEG antibodies are present in the sample or if the titer of human IgG anti-PEG antibodies in the sample is above a threshold level. |
| 27. The method of any of Embodiments 24-26 wherein the threshold level of human IgG anti-PEG antibodies is the lowest level at which:<br>a. the PEGylated therapeutic compound is rendered ineffective for treatment; or<br>b. the side-effects of the anti-drug response to the PEGylated therapeutic compound outweigh the benefits of treatment. |

The present disclosure is further illustrated by the following examples, which should not be construed as further limiting. The contents of all figures and all references, Genbank sequences, patents and published patent applications cited throughout this application are expressly incorporated herein by reference.

EXAMPLES

Example 1

Antibody Generation

Monoclonal Anti-PEG Antibodies:

Mice were immunized with a panel of PEGylated therapeutic compounds and hybridomas were selected that showed binding to PEG coupled to unrelated proteins thus ensuring anti-PEG reactivity. The therapeutic proteins used as immunogens as well as PEGylated proteins used in the screening assays were chemically linked to a branched 40 kD PEG. Monoclonal hybridoma cell lines were derived and two antibodies were identified based on their specificity and affinity to PEG indirectly derived in direct binding assays. The variable region genes from these two cell lines were sequenced, subcloned into human IgG1 Fc bearing constructs, stably expressed in CHO cell lines and purified. These are therefore referred to as chimeric anti-PEG antibodies PEG.1 and PEG.2 monoclonal antibodies (mAb) since they retain their mouse variable region with a human IgG Fc1. Reengineering the monoclonal antibodies with a human IgG Fc did not affect its reactivity to PEG—both the chimeric and native hybridoma IgG had similar binding to PEG. Nucleic acid and polypeptide sequences for antibodies PEG.1 and PEG.2 and their variable domains are provided at SEQ ID NOs: 1-14. Most of the assay format evaluations and characterization were done on the PEG.2 since it had slightly better binding than the PEG.1 chimeric antibody.

Polyclonal Bovine Antibodies:

Human IgG transchromosomal (Tc) cows at Sanford Applied Biosciences, Sioux Falls, S. Dak. (Kuroiwa et al. (2009) *Nat. Biotechnol.* 27:173) were immunized with either KLH chemically conjugated to 5 kD PEG or with a mix of PEGylated therapeutic molecules. While the KLH-conjugated PEG had a far higher number of PEG molecules coupled to each KLH, the therapeutic molecules typically had a single 20-30 kD PEG attached to a protein. This system enabled generation of PEG specific polyclonal antibodies similar to the monoclonal chimeric antibodies, but bearing both the Fc and Fab from human IgG. Cows were immunized at monthly intervals and sera were tested for both anti-PEG and anti-protein reactivity. Animals with the highest anti-PEG titers as determined in a direct binding assay to two PEGylated therapeutics were selected for plasmapheresis. Anti-PEG reactivity was tested in a generic assay format using the crude serum, purified total IgG and PEG affinity purified IgG. Of the three cows used in the immunization protocol, plasma from cow #2026 was selected based on its titer to two PEGylated therapeutic molecules—for further affinity purification and further characterization of the anti-PEG polyclonal antibody (pAb).

Generation of Anti-PEG IgG:

Immunization using PEG-conjugated therapeutic molecules or with KLH-PEG successfully resulted in the formation of PEG reactive IgG in the animals. FIG. 1A shows markedly different seroreactivity from three different bovines. These results were also confirmed by binding experiments using a second PEGylated therapeutic (FIG. 1B) Titers in general peaked after 2-3 boosters discounting any merit in further boosters unlike standard immunization regimes for protein-specific antibodies. We also observed better titers in response to KLH conjugated PEG than to PEGylated therapeutic molecule immunizations. This could be attributed to the availability of far higher amounts of PEG on a molar basis in the KLH preparations than in the one PEG to one protein conjugates with therapeutic molecules.

Example 2

Purification of Anti-PEG Polyclonal Antibodies

PEG Affinity Resin Preparation:

5K PEG-$CH_3O(CH_2CH_2O)n(CH_2)_2SH$ (Sunbright ME-0505H, NOF) was solubilized in water to 100 mg/ml with 5 mM TCEP. PD-10 desalting column was used to exchange to PBS buffer, pH 7.5 and remove TCEP right before conjugating to SulfoLink Coupling resin (Thermo Scientific). Conjugation was allowed to occur at ambient temperature for one hour. The ratio of 5K PEG to resin was about 1 mg PEG per ml resin. Higher amount of PEG per ml resin did not provide higher binding capacity in purifying anti-PEG polyclonal antibodies. The PEG coupled resin was incubated with excess amount of L-cysteine solution for one hour to block unused iodoacetyl groups.

Purification of Anti-PEG Polyclonal Antibodies:

500 ml of bovine plasma was first passed over Mab Select Protein A Affinity resin (GE Healthcare) which yielded approximately 3.5 grams of total IgG antibodies and was neutralized to pH 7. Anti-PEG polyclonal antibodies (pAbs) typically had mild to moderate binding to PEG affinity resin. Multiple batch purification processes were needed to completely recover anti-PEG antibody from total antibody. Since batch purification enabled longer contact time, the PEG affinity resin was incubated with total IgG with gentle stirring at ambient temperature for one hour. The suspension was poured into an appropriate Econo-column (Bio-Rad) and flow through was carefully collected. The resin was washed thoroughly by PBS buffer and the antibodies eluted by low pH solution of 50 mM sodium acetate, pH 2.7 and immediately neutralized by 1 M Tris, pH 8. The binding capacity of the resin to anti-PEG pAbs 127 was around 2.5 to 3.0 mg/ml resin. Flow through (FT) was evaluated for any residual anti-PEG activity and repeatedly passed over the column until most of the reactivity in the FT was eliminated. Around 80 mgs of anti-PEG antibody were obtained by PEG affinity purification. Higher molecular weight aggregated antibody, which accounted for about 40% of total IgG, was removed by Superdex 200 sizing-exclusion column. The remaining 40 mgs of monomeric antibody was purified from size exclusion column in PBS buffer, and concentrated to 3 mg/ml, aliquoted and frozen in −80 Celsius. Unlike typical chromatographic purifications of anti-protein antibodies multiple batch purifications were needed overcome the poorer affinity to maximize extraction of anti-PEG antibodies from total antibodies.

Purification of the polyclonal anti-PEG antibodies using PEG affinity chromatography resulted in a relatively lower yield of purified IgG than what would have been expected from an immunogenic protein. Antibody sample was stable for at least 4 weeks in 4° C. following one freeze thaw cycle. Preliminary analysis by mass spectrometry indicated approximately ten different antibodies in the polyclonal mixture at detectable levels (data not shown). The purified polyclonal antibodies also had a high content of aggregates that had to be separated and thus lowering the final yield.

Example 3

Comparison with Commercial Anti PEG Antibodies

Rabbit monoclonal anti-PEG antibody (B-47) was purchased from Epitomics, San Francisco and mouse monoclonal anti-PEG IgG (6.3) and IgM (AGP4) from Abnova (original clone developed at Academia Sinica). These were used in comparison with our custom antibodies for specificity testing. Product specification information from the providers indicated mCap specificity for the B-47 and backbone specificity for the 6.3 clone.

The properties of the antibodies of the present invention are compared with selected commercial anti-PEG antibodies in Table 2.

TABLE 2

Characteristics of Evaluated Anti-PEG IgG Antibodies

| Name | PEG.1 | PEG.2 | # 2026 | B-47 | 6.3 |
|---|---|---|---|---|---|
| Source | This work | This work | This work | Commercial | Commercial |
| Immunized animal species | Mouse | Mouse | Transchromosomal Bovine | Rabbit | Mouse |
| Type | Monoclonal chimeric IgG | Monoclonal chimeric IgG | Polyclonal human IgG | Monoclonal rabbit IgG | Monoclonal mouse IgG |
| Heavy chain | Human IgG1 | Human IgG1 | Human | Rabbit | Mouse |
| Light chain | Mouse | Mouse | Mostly bovine | Rabbit | Mouse |
| Specificity | N/A | Backbone subunit dependent on secondary length | Backbone subunit independent of secondary length | Methyl cap with adjoining subunits | Backbone subunit independent of secondary length |
| Affinity | N/A | Varies with PEG MW | Varies with PEG MW | High | N/A |
| MW of PEG giving preferential binding | N/A | Moderate to larger | Smaller to moderate size | N/A | N/A |

Example 4

Biotin-Conjugated PEG

Biotin was conjugated to 40 kD branched PEG using maleimide-thiol chemistry. 40K-branched-PEG-Mal (NOF#GL2-400MA01, lot G08903, mol wt=42 kD) was prepared at 13.5 mg/ml in 20 mM sodium phosphate pH 7.0/150 mM NaCl. N-biotinyl-Cysteine (Carbosynth #FB154460, lot FB1546001201, MW=347) was prepared at 10 mg/ml in DMSO. A 21-fold excess of Cys-biotin was added to 40K-PEG-Mal and mixed for 2 hrs at room temp. The sample was brought to 5 ml with phosphate buffer and then dialyzed twice against 2 L of DPBS to remove free CYS-biotin. To verify conjugation, the sample pre and post biotin reaction was run on non-reduced SDS-PAGE, blotted onto nitrocellulose membrane, blocked with 1% BSA-PBS-Tween (Teknova#D5120), probed with Streptavidin-HRP (Pierce #21126) at 1 μg/ml, and reacted with HRP substrate (BioRad). A band in the post-reaction sample of the same MW as the stained PEG (70K) reacted with the Streptavidin-HRP while the pre-conjugate PEG-Mal and cysteine-conjugated control did not react with Streptavidin-HRP. PEG molecules of various molecular weights conjugated to biotin were purchased from Nanocs (www.nanocs.net). These varied from 350 daltons to 40 kD PEG (Cat # PGI-BN 350, 550, 750, 1k, 2k, 5k, 10k, 20k, 30k, 40k).

Example 5

SPR Analysis of Anti-PEG Binding to PEG

Neutravidin was purchased from Thermo Scientific (Rockford, Ill., USA). Ethanolamine hydrochloride, N-hydroxysuccinimide (NETS), and 1-ethyl-3-(3-dimethylaminopropyl) carbodiimide (EDC) were purchased from Sigma-Aldrich (St. Louis, Mo., USA). The regeneration buffers (10 mM glycine-159 HCl at pH 3.0, 2.5, 2.0, and 1.5), the HBS-N running buffer (10 mM HEPES, pH 7.4, 150 mM NaCl), the immobilization buffer (10 mM sodium acetate buffer, pH 5.0), and the series S CMS sensor chips used for SPR experiments were purchased from GE Healthcare (Piscataway, N.J., USA). A Biacore T200 SPR instrument (GE Healthcare, Piscataway, N.J., USA) was used to study the binding interactions between the biotinylated PEGs and the anti-PEG antibodies.

Immobilization of Biotin-PEG onto a Neutravidin-Coated Sensor

Immobilization of neutravidin onto the CMS sensor was achieved using the wizard template method in the Biacore T200 control software (version 1.0) with a target immobilization level of 5000 response units (RUs). Typically, two flow cells of a CMS sensor were pretreated with an injection of 50 mM NaOH (30 μL at 30 μL/min) to remove any nonspecifically bound substances. A freshly prepared mixture of EDC (400 mM) and NHS (100 mM) was injected (10 μL/min) onto both flow cells for 7 min to activate the carboxyl groups on the surface. Neutravidin (50 μg/mL in 10 mM sodium acetate buffer at pH 5.0) was then injected onto both flow cells at short pulses (12 sec to 6 min at 5 μL/min) to ensure the target immobilization level reached. Finally, excess active groups on both flow cells were blocked with an injection (10 μL/min) of 1 M ethanolamine, pH 8.0, for 7 min. The surface was conditioned with three injections of 50 mM NaOH/1 M NaCl followed by another three injections of 10 mM glycine-HCl at pH 1.5 (10 μL of each injection at 10 μL/min) prior to the immobilization of the biotin-PEG. Biotin-PEG was immobilized onto one flow cell by multiple short injections (18 s per injection) of the biotin-PEG at 5 μL/min to achieve the target immobilization level.

SPR Binding Analysis

Typically, 120 μL of anti-PEG antibody at three different concentrations (100, 300 and 1000 nM) in the HBS-N running buffer was injected onto both flow cells at a flow rate of 30 μL/min. At the end of the sample injection, the running buffer was flowed over the sensor surface for 10 min to allow dissociation. After dissociation, the sensor surface was regenerated for the next sample concentration by injecting 15 μL of 10 mM glycine-HCl, pH 1.5, at 30 μL/min. Anti-PEG antibody at 100 mM was injected twice to ensure reproducibility. Blank (running buffer) injections were performed in intervals after several sample injections for the purpose of double referencing calculation during data analysis. The sample solutions were flowed over the control flow cell and the PEG-immobilized flow cell in sequence, and the responses were monitored as a function of time at 25° C. Binding RUs of each antibody to each PEG molecule at the end of the association phase were reported in the Biacore T200 control software (version 1.0).

Example 6

MSD Analysis of Anti-PEG Binding to PEG

Direct assay on Meso Scale Discovery platform was performed as follows. Biotin-PEG was coated on Streptavidin MSD plates at a concentration of 2 μg/mL in assay buffer which was a commercially obtained StartingBlock™ (PBS) Blocking Buffer without Tween 20 (Thermo Scientific, Rockford, Ill., catalog #37538). Plates were washed and blocked with the same buffer before adding samples containing anti-PEG antibodies. Calibrators and quality control samples were prepared in assay buffer using either PEG.2 mAb or #2026 pAb. The starting block buffer was also used as assay buffer for all reagent dilutions. Samples were allowed to incubate on the plates for 2 hrs before washing 5 times with wash buffer containing no Tween 20. The bound anti-PEG antibodies were detected using ruthenylated tagged mouse anti-human IgG monoclonal antibody R10Z8E9 from the University of Birmingham, UK (ST-R10). Conjugation of R10 antibody with the sulfotag label was done using standard protocols provided by MSD and a single lot was used for comparative purposes across all experiments. Following incubation with ST-R10 for 30 minutes, the plates were washed as in the earlier step. Freshly prepared MSD Read Buffer T (4×) with Surfactant (catalog #R92TC-2) was added to the wells and read on Sector Imager 2000.

Semi Homogenous Assay on MesoScale Discovery Platform.

Biotin-PEG at a fixed optimized concentration was incubated with a titration of anti-PEG antibodies in solution allowing the antibody binding with the PEG molecule to occur in solution. Following an incubation of the mix for 2 hrs on a shaking platform, a portion of the mix was added to pre-blocked Streptavidin coated MSD plates. Unbound material was washed and the bound complexes on the plate were detected using ST-R10. The plates were read thereafter on a sector imager 2000. Ratio and concentration of the labeled materials were optimized depending on the MW of the PEG. The assay was developed using 2 μg/mL of biotin tagged PEG and 1 μg/mL of the ST-R10 antibody. The titrations for both the PEG.2 mAb and #2026 pAb were compared at the same range.

Detection of anti-PEG antibodies may also be performed using the Acoustic Membrane MicroParticle (AMMP®) magnetic microparticle-based detection assay, as described at Dong et al. (2015) *AAPS J.* 17:1511.

Example 7

PEG Molecular Weight Dependence of Anti-PEG Antibody Binding

Figure 3:
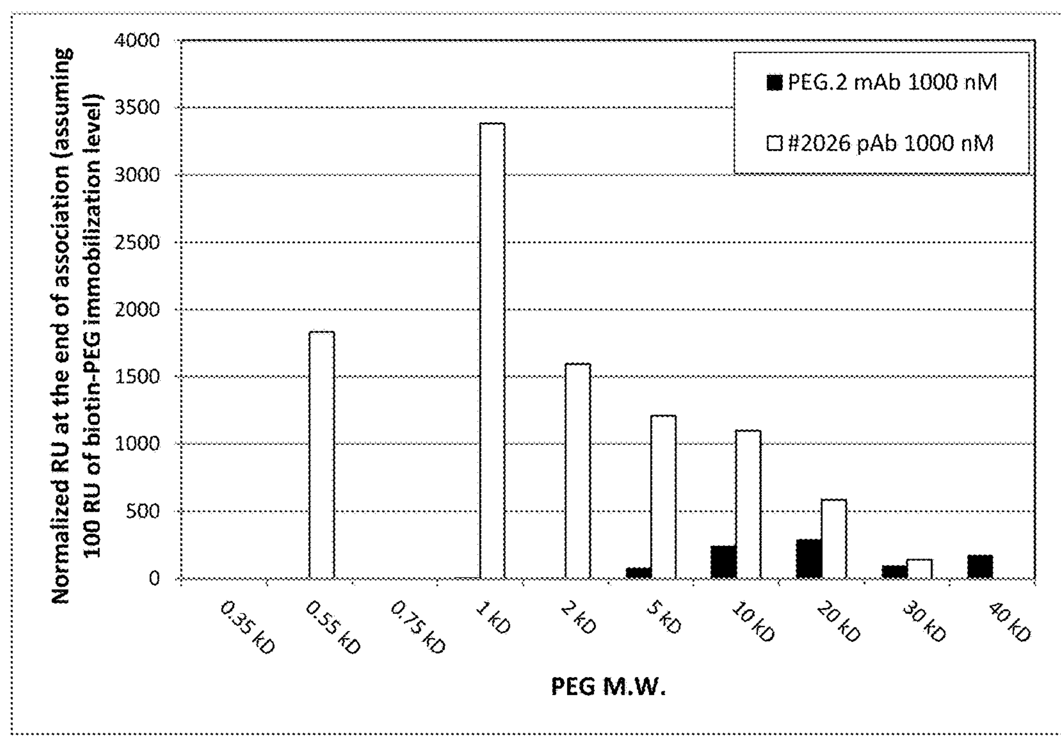
FIG. 3 shows the differential effect of PEG MW on binding by two anti-PEG antibodies of the present invention as determined by SPR. See Example 7.
Figure 4A:
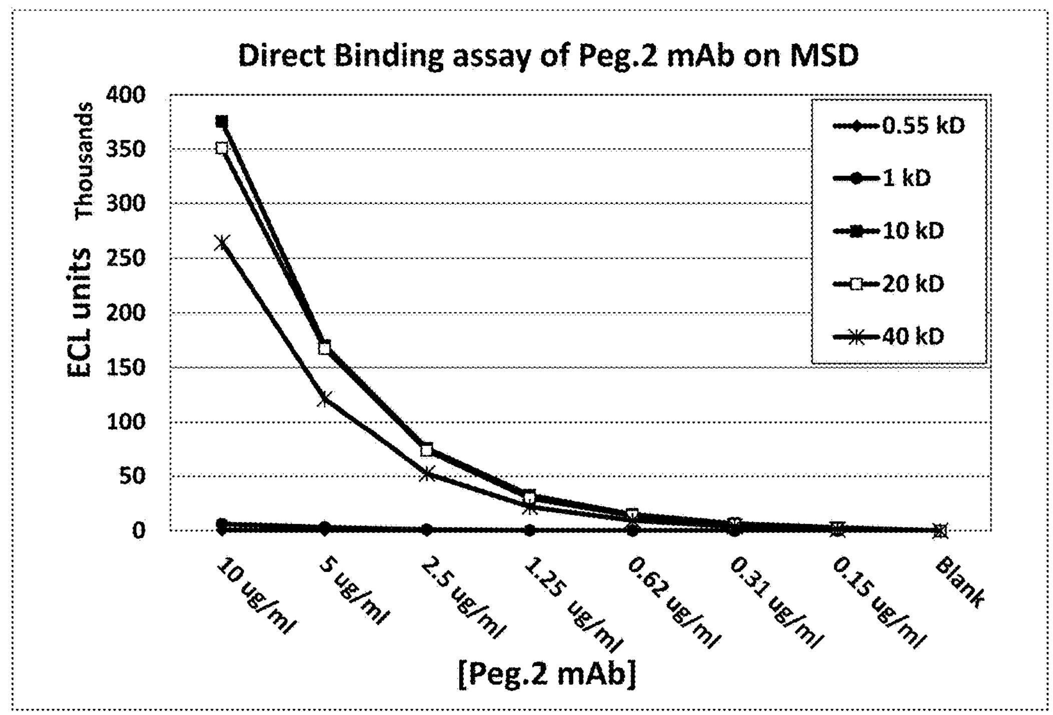
FIGS. 4A, 4B, 4C and 4D show titration of PEG.2 mAb and #2026 pAb anti-PEG antibodies in buffer using multiple assay formats (direct binding assay or solution based assay, as indicated) as a function of PEG molecular weight, showing the influence of PEG MW on antibody binding. See Example 7.
Figure 4B:
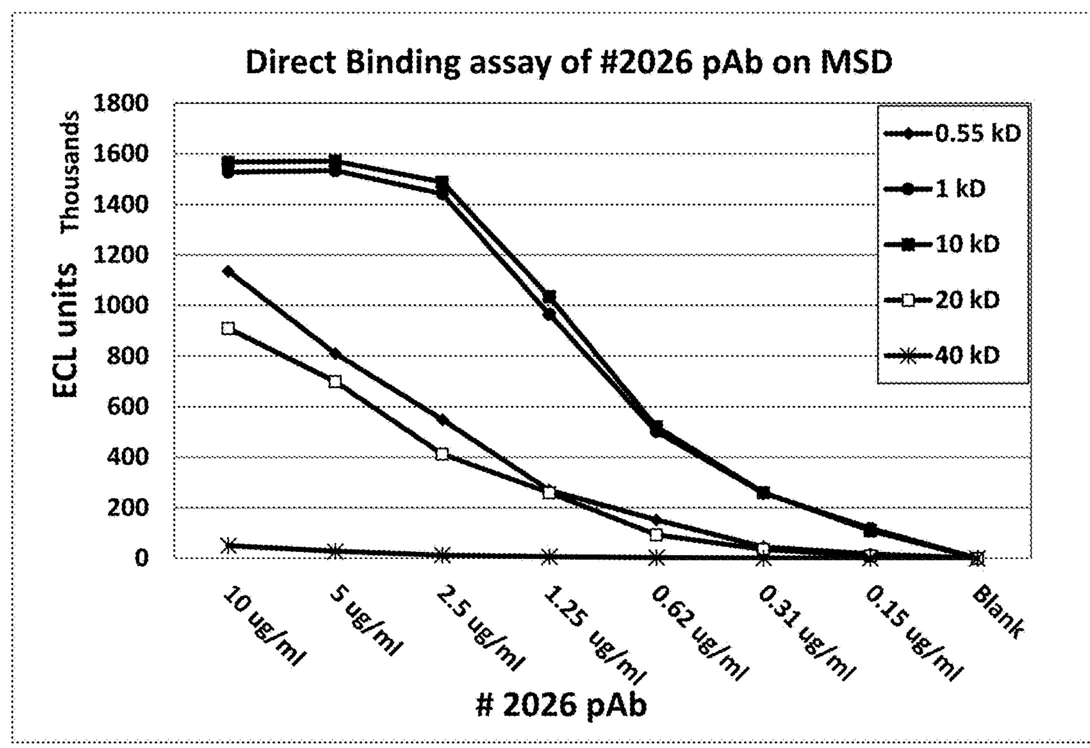
Figure 4C:
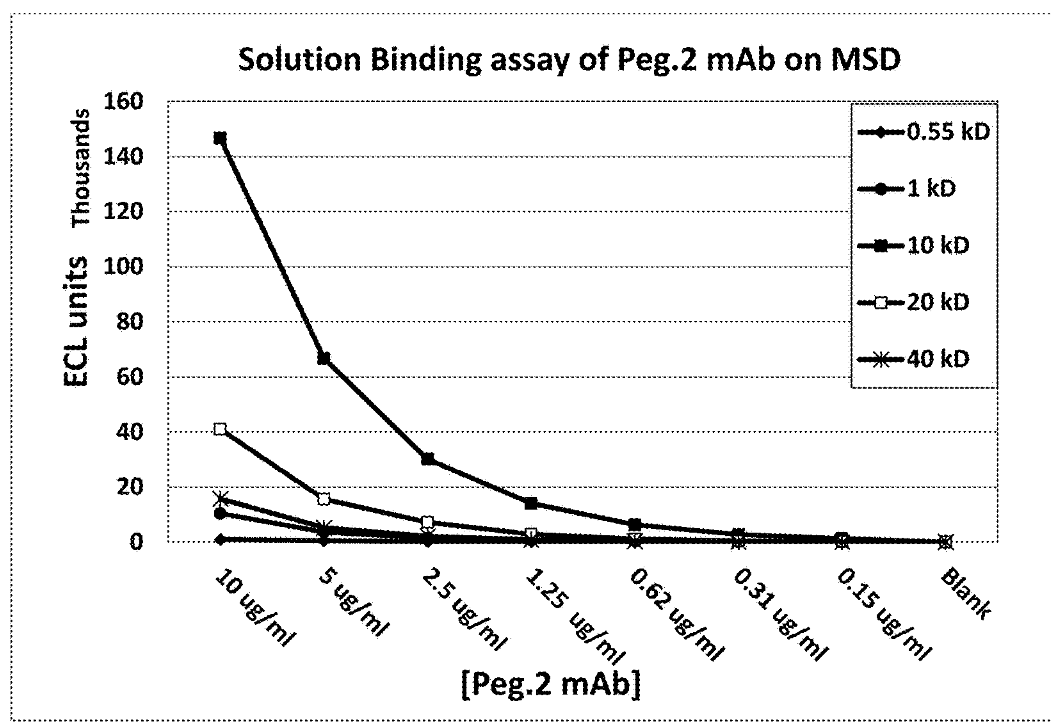
Figure 4D:
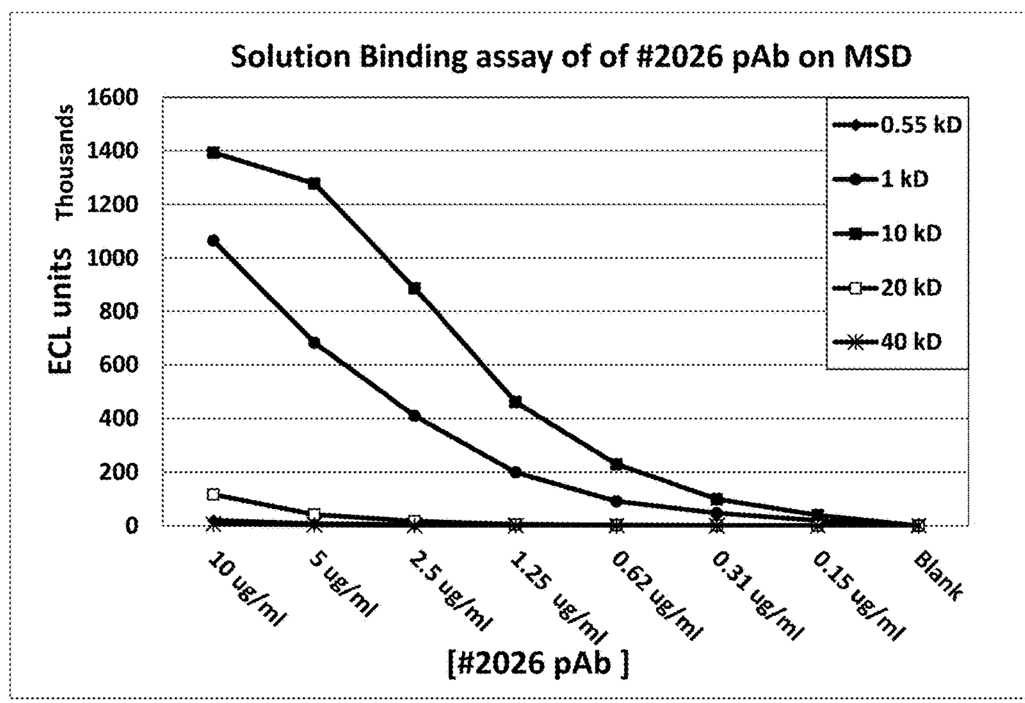

The PEG molecular weight (MW) dependence of anti-PEG antibody binding was studied in SPR binding experiments. During the experiments, short injections (18 seconds) of the biotin-PEG were performed to ensure that similar RU was achieved across the PEGs with different MWs. Therefore, similar mass of ligand was achieved across the ten PEGs studied in this work. It should be noted that the absolute moles of PEG immobilized were inversely proportional to the size of the PEG molecule. However, the immobilization level was similar in terms of the total number of ethylene oxide subunits. Three concentrations of each anti-PEG antibody (1000, 300 and 100 nM) were used to study the binding interaction with the PEG at each MW. Anti-PEG antibody at 100 mM was injected twice and used to evaluate binding reproducibility of the assay. The overlaid sensorgrams obtained from the duplicate runs demonstrate good binding reproducibility. FIG. 3 illustrates the binding RU of each antibody (1000 nM) to each PEG molecule at the end of the association phase. For better comparison of the binding across the ten PEGs, the RUs were normalized assuming that an immobilization level of 100 RU was achieved for each biotin-PEG. As shown in FIG. 3, the PEG.2 mAb showed the highest normalized binding RU to the 20-kDa PEG, while the #2026 pAb shows the highest RU to the 1-kDa PEG. This result was consistent with the binding pattern observed from the plate-based assays where the PEG.2 mAb had a preferential binding for the larger sized PEG and the #2026 pAb preferred the small to intermediate sized PEG. It should be noted that the RU observed for the #2026 pAb binding to each PEG was higher than the one observed for the PEG.2 mAb, again consistent with the plate based assays. Assuming a 1:1 binding interaction between the PEG and the anti-PEG antibody, none of the binding RUs observed for the polyclonal antibody exceeded the binding capacity of each PEG immobilized on the sensor surface. The unexpected low binding RU observed for PEG.2 indicated that the monoclonal antibody had very limited access to the PEG molecule immobilized on the sensor surface and its binding may require a secondary structure of the PEG which may not be available after immobilization. Both the monoclonal and the polyclonal antibodies were identified to have fast binding off-rates to the PEG molecules. This was apparent for the 30-kDa PEG where the binding sensorgrams of both antibodies went back to the baseline at the end of the 10-min dissociation phase. Significant negative binding RUs were observed for the interaction between the 40-kDa PEG and the polyclonal antibody at the three concentrations studied in this work. A possible reason for this is that binding of the polyclonal antibody to the 40-kDa polymeric PEG molecule may change the local SPR performance at the sensor surface and may interfere with the SPR detection by forming a binding complex.

Binding of Anti-PEG Antibodies to Various Size PEG Molecules

A monoclonal antibody (PEG.2) and a polyclonal antibody (#2026) were selected for evaluation of their binding to PEG as these were the best binders from the panel of antibody preps that we screened. We looked at their binding to both immobilized PEG coated on a plate as well as to PEG in solution. Furthermore we also asked whether the molecular size of the linear PEG molecule influenced the binding.

Figure 5:
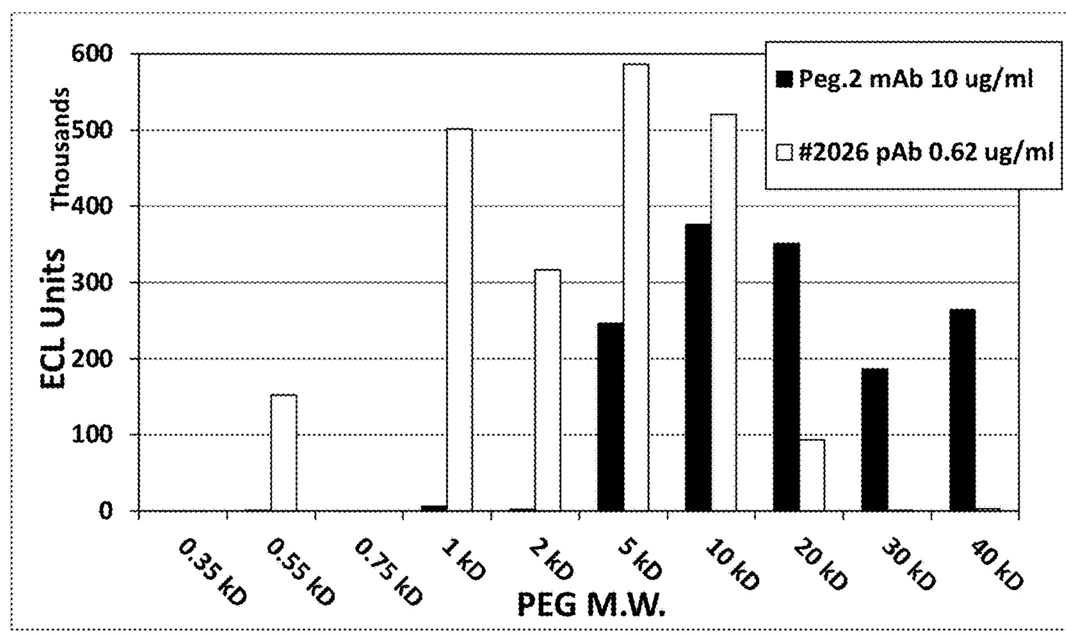
FIG. 5 shows differential effect of PEG MW on binding by two anti-PEG antibodies of the present invention as determined by MSD methods. See Example 7.

Our initial binding data was confirmed using 40 kD PEG, typical of several PEGylated biotherapeutics. However, in light of the fact that most ubiquitously present PEG in food and cosmetic products tend to be of smaller MW, the binding characteristics of these antibodies were also tested using PEG<5 kD in size. Initial screening experiments indicated a profound divergence in the binding profiles of the antibodies to PEG of 40 kD and 550 daltons sizes. This led us to explore binding to PEG molecules of intermediate sizes as well. FIGS. 4 and 5 summarize the titration data from five selected PEG molecules of different MW using the two anti-PEG antibodies. Since coating plates with PEG molecules could create binding artifacts due to altered shape or epitope masking, we confirmed our findings from the direct assay with a solution based specificity experiment. Both direct (FIGS. 4A-4B) and solution phase binding (FIGS. 4C-4D) for any given antibody demonstrated a consistent binding pattern to PEG molecules of varying molecular weights. Overall the data indicated a preference by the PEG.2 mAb for the larger sized PEG and by the #2026 pAb for a smaller to intermediate size PEG. The comparative binding data of these two antibodies to various PEG molecules are shown in FIG. 5. The comparison was done using two different concentrations of the two antibodies to account for the profound differences in their binding signal intensity as seen on the PEG molecules.

Example 8

Epitope Specificity of Anti-PEG Antibody Binding

We next investigated whether the differential profiles reflected differences in antibody specificity to binding epitopes on the PEG. A competition assay format with inhibitors containing specific epitopes was chosen to differentiate the anti-PEG antibodies (commercially available and antibodies disclosed herein). The triethylene glycol monomethyl ether (mTEG) from Sigma Aldrich Corp (Atlanta, Ga., catalog #90450-250ML) with linear formula $CH_3(OCH_2CH_2)_3OH$ and MW 164.20 (FIG. 2) was used to determine specificity to the methyl-cap termini of PEG including only a few linear ethylene oxide subunits. Amine-PEG-amine (aPEGa) from Creative PEGWorks (Winston Salem, N.C., catalog # PSB-335) with the linear formula $NH_2(CH_2)_2O(CH_2CH_2O)_n(CH_2)_2NH_2$ and MW 20,000 has like any PEG molecule a normal distribution around a mean of 454 ethylene oxide subunits (FIG. 2) and was used to determine specificity to the PEG backbone. Differential inhibition by both competitors was used to indicate whether an antibody binding to the ethylene oxide subunit was dependent on the secondary structure of the PEG backbone. The binding was tested in two experimental formats; the direct binding format where biotin-PEG was first immobilized on a streptavidin plate followed by antibodies to bind; in the second semi-homogeneous format the biotin PEG was incubated with the antibodies in buffer and then the complex was captured on a Streptavidin plate. Four antibodies, (PEG.2 mAb, #2026 pAb, B-47 and 6.3), were titrated and incubated with five concentrations of a competitor, as well as without competitor.

Direct Binding Format on MesoScale Discovery Platform

In the direct binding competition assay, biotin-PEG at 20k MW was coated on Streptavidin Gold plates (MesoScale Discovery, Rockville, Md., catalog # L15SA-1) at a concentration of 2 μg/mL in Dulbecco's Phosphate Buffered Saline (PBS) (Lonza BioWhittaker®, Walkersville, Md., catalog #17-512Q). Plates were washed with PBS (Sigma-Aldrich, St. Louis, Mo., catalog #P4417-100TAB) and blocked with StartingBlock™ (PBS) Blocking Buffer. Samples were prepared in StartingBlock™ buffer with and without individual competitors and an anti-PEG antibody (PEG.2 mAb, #2026 pAb, B47 mAb and 6.3 mAb) and allowed to incubate for one hr at room temperature with shaking for binding to competitors to occur. The blocked plate was washed five times with PBS, after the samples were allowed to incubate on the plates for 1.5 hrs followed by washing five times with PBS. The bound anti-PEG antibodies were detected using the appropriate ruthenylated anti-species antibody (mouse anti-human IgG monoclonal antibody R10Z8E9 from the University of Birmingham, UK, goat anti-mouse or goat anti-rabbit polyclonal antibodies from MSD) during one hr incubation, followed by washing five times with PBS. MSD Read Buffer T (4×) with Surfactant (catalog #R92TC-2) prepared fresh at a 1× concentration was added to the plates and read on the SECTOR Imager 6000.

Semi-Homogenous Format on MesoScale Discovery Platform

Biotin-PEG (20k MW) at 2 μg/mL was incubated with a titration of an anti-PEG antibody (PEG.2 mAb, #2026 pAb, B47 mAb and 6.3 mAb) and a competitor in solution allowing the antibody to bind with the PEG molecule or the competitor in solution. Following a two hour incubation of the mix on a shaking platform at room temperature, a portion of the mix was added to pre-blocked Streptavidin Gold plates (MSD). Unbound material was washed with PBS and the bound complexes on the plate were detected using 1 μg/mL of the appropriate ruthenylated anti-species antibody (mouse anti-human IgG monoclonal antibody R10Z8E9 from the University of Birmingham, goat anti-mouse or goat anti-rabbit polyclonal antibodies from MSD). Following five washes with PBS, MSD Read Buffer T (4×) with Surfactant (catalog #R92TC-2) prepared fresh at a 1× concentration was added to the plates and read on the SECTOR Imager 2000.

Specificity

Specificity of most commercial anti-PEG antibodies are classified either to methyl cap on the PEG (mCap) or to the backbone composed of ethylene oxide subunits; this was the basis for investigating specificity of our in house antibodies. Tween-20 in the wash and assay buffers interfered with the binding of antibodies that were specific to the backbone indicating cross reactive epitopes. Thus, we eliminated this detergent from all experimental steps.

Figure 2:
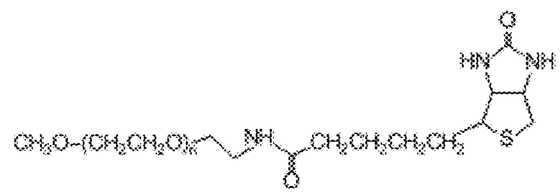
FIG. 2 provides chemical structures for various materials of the present invention.

Since direct binding results suggested that the size of the PEG backbone might influence specificity to the backbone, we used two competitors. The first consisted of a methyl cap forming a methyl ether bond with just three ethylene oxide subunits and the second competitor a 20 kD MW PEG that had no terminal methyl ether bonds but instead the terminal hydroxyls on both ends were capped by an amine group ($H_2N—O—(CH_2CH_2O)_n—NH_2$) (FIG. 2). In order to differentiate influence of long polymerized subunits from separated subunits on the binding, the number of ethylene oxide subunits was normalized to one another for determination of inhibitor concentration. In addition, the competitors were tested at 10-fold lower, and 10-, 100- and 1000-fold higher to biotin-mPEG. Inhibition of binding in the presence of competitors was compared and used to ascertain whether an antibody showed specificity to 1) the methyl cap (inhibition with mTEG but no inhibition with $H_2N—O—(CH_2CH_2O)_n—NH_2$ at any ratio) 2) the methyl cap and adjacent linear ethylene oxide subunits (stronger inhibition with mTEG and some inhibition with $H_2N—O—(CH_2CH_2O)_n—NH_2$), 3) the ethylene oxide subunits in the backbone independent of secondary structure (similar inhibition with mTEG and with $H_2N—O—(CH_2CH_2O)_n—NH_2$) or 4) the ethylene oxide subunits in backbone but dependent on some secondary structure (stronger inhibition with $H_2N—O—(CH_2CH_2O)_n—NH_2$ than with mTEG).

Figure 8A:
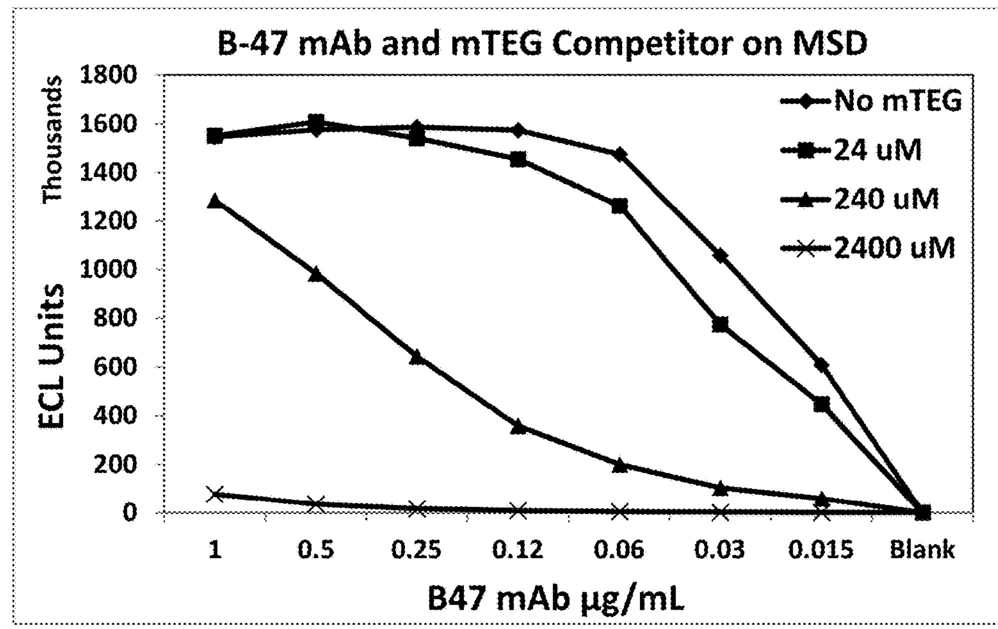
FIGS. 8A and 8B show titrations of anti-PEG mAb B47 in buffer using direct assay format showing the influence of competitors mTEG and aPEGa, respectively. See Example 8.
Figure 8B:
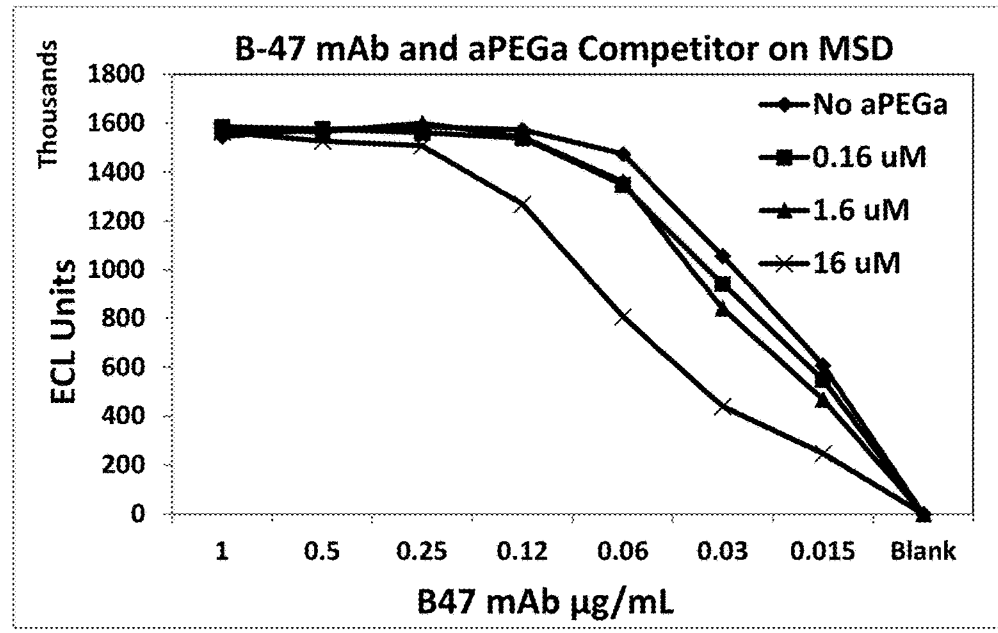
Figure 9A:
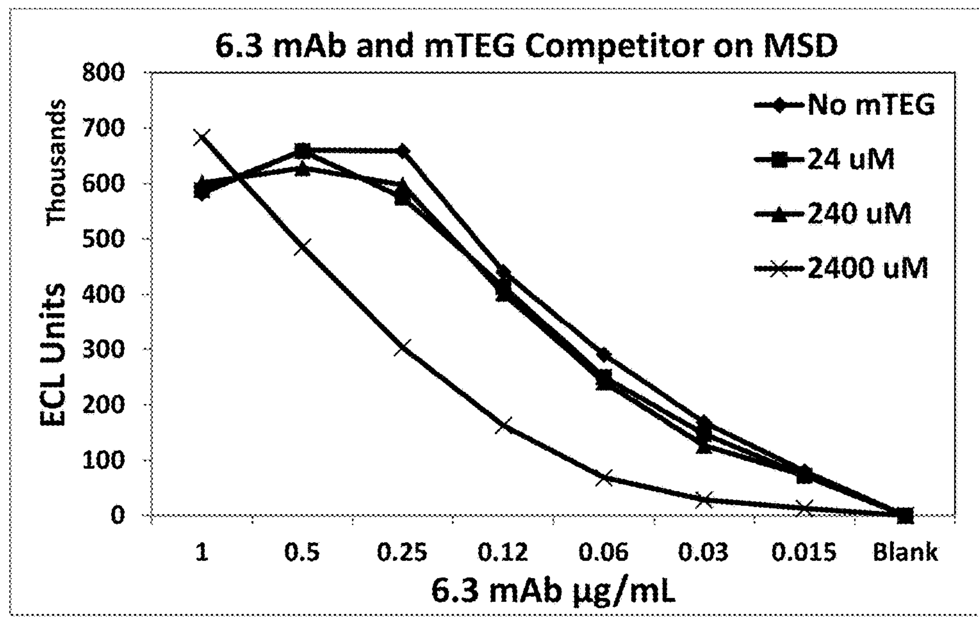
FIGS. 9A and 9B show titrations of anti-PEG mAb 6.3 in buffer using direct assay format showing the influence of competitors mTEG and aPEGa, respectively. See Example 8.
Figure 9B:
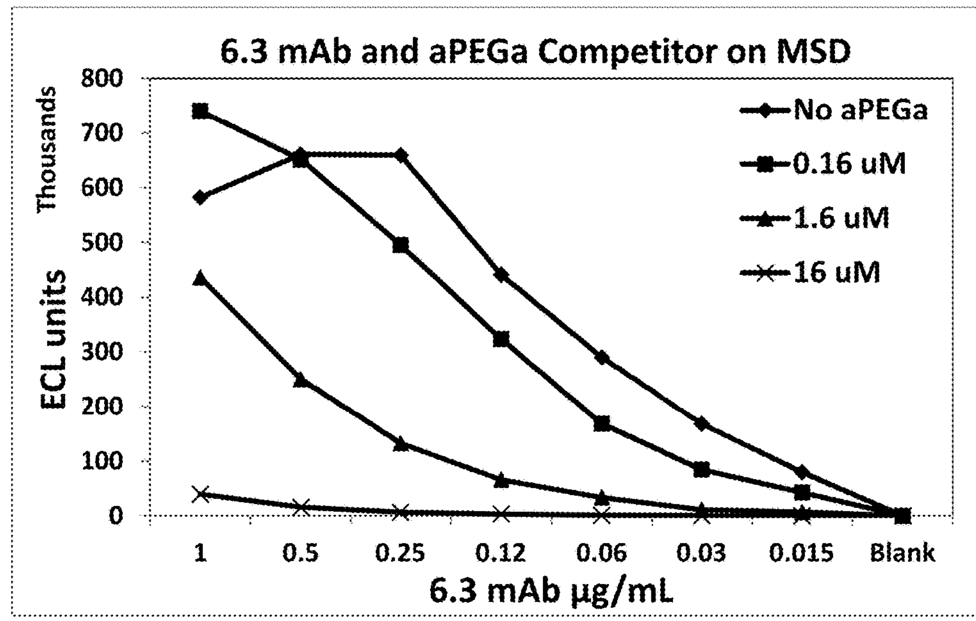

Two commercial antibodies with specificities provided by the manufacturer were used to test the validity of our approach to specificity determination. A rabbit monoclonal antibody B-47 described as having methyl cap specificity and a mouse monoclonal antibody 6.3 with high affinity for the PEG backbone were evaluated. There was stronger binding and better resolution of inhibition during competitor titration in the direct assay format than in semi homogeneous format. This was probably due to the epitopes on PEG being in closer proximity on solid surface which would help binding to antibodies with inherently faster off rates by limiting their diffusion. While inhibition of the commercial rabbit monoclonal antibody B-47 was far greater with mTEG than $H_2N—O—(CH_2CH_2O)_n—NH_2$ as expected from its methyl cap specificity, it was interesting to note some cross reactivity to $H_2N—O—(CH_2CH_2O)_n—NH_2$ at higher concentrations in the direct format assays suggesting the antibody probably also recognizes some backbone subunits most likely adjacent to the methyl cap. The conclusion that B-47 mAb is purely methyl-cap specific was therefore not consistent with our direct binding assay data. For the commercial monoclonal antibody clone 6.3, there was far greater inhibition with $H_2N—O—(CH_2CH_2O)_n—NH_2$ than mTEG at equivalent subunits; while inhibition by $H_2N—O—(CH_2CH_2O)_n—NH_2$ was observed starting at an equivalent number of subunits of competitor to biotin-PEG level, mTEG competitor needed to have at least 100-fold excess subunits over biotin-PEG. This indicated that 6.3 clone is backbone subunit specific and most likely dependent on secondary structure. The differences in the two inhibitors at various amounts were better evident in the direct (FIGS. 8 and 9) than in the semi homogeneous format (data not shown).

Figure 6A:
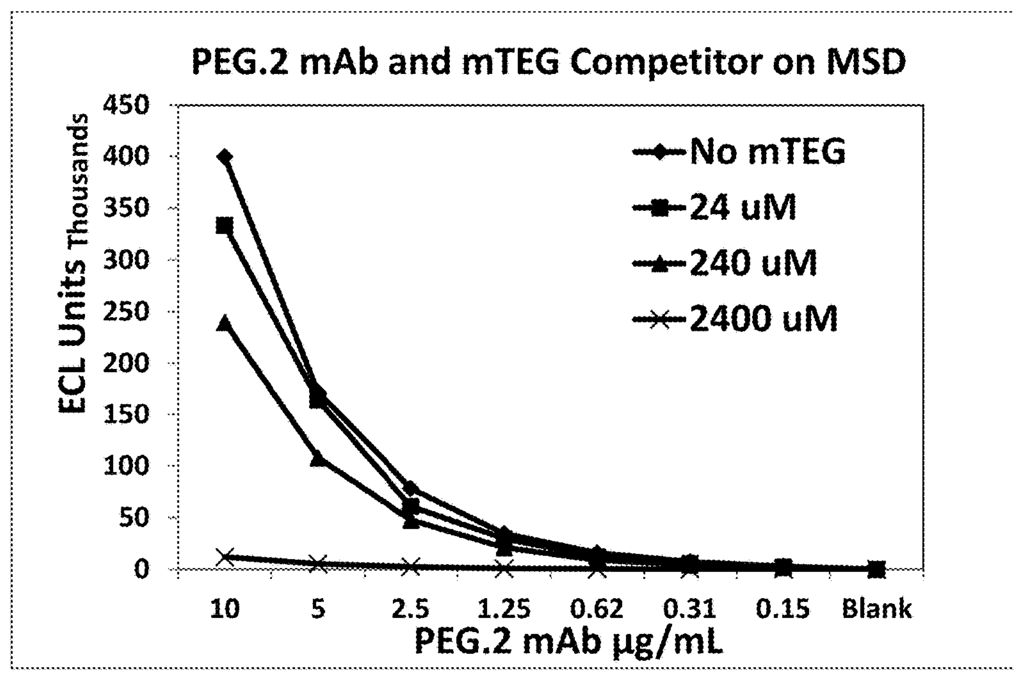
FIGS. 6A and 6B show titrations of anti-PEG mAb PEG.2 in buffer using direct assay format showing the influence of competitors mTEG and aPEGa, respectively. See Example 8.
Figure 6B:
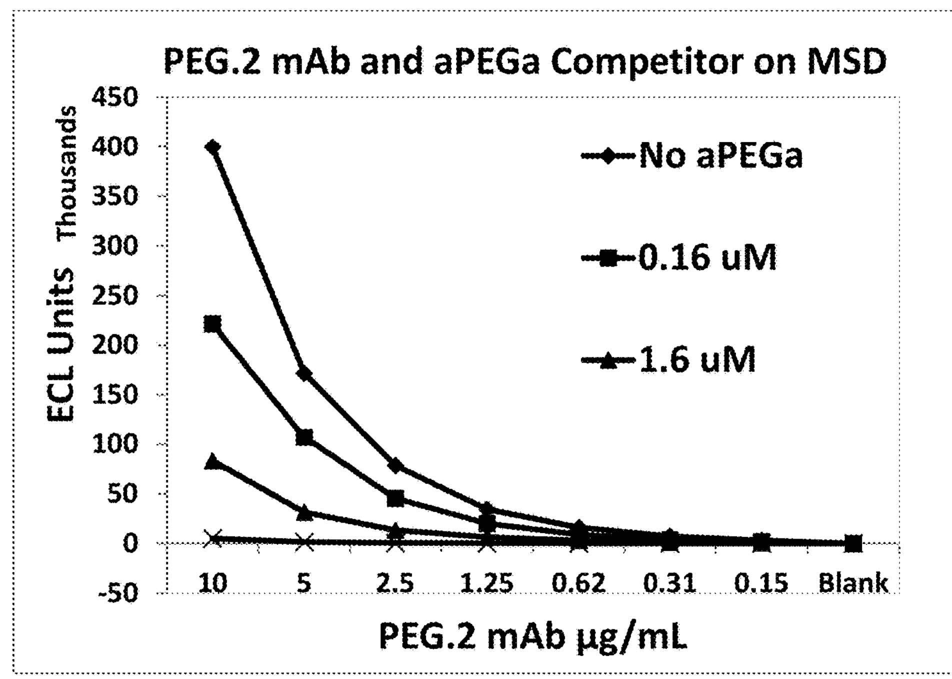
Figure 7A:
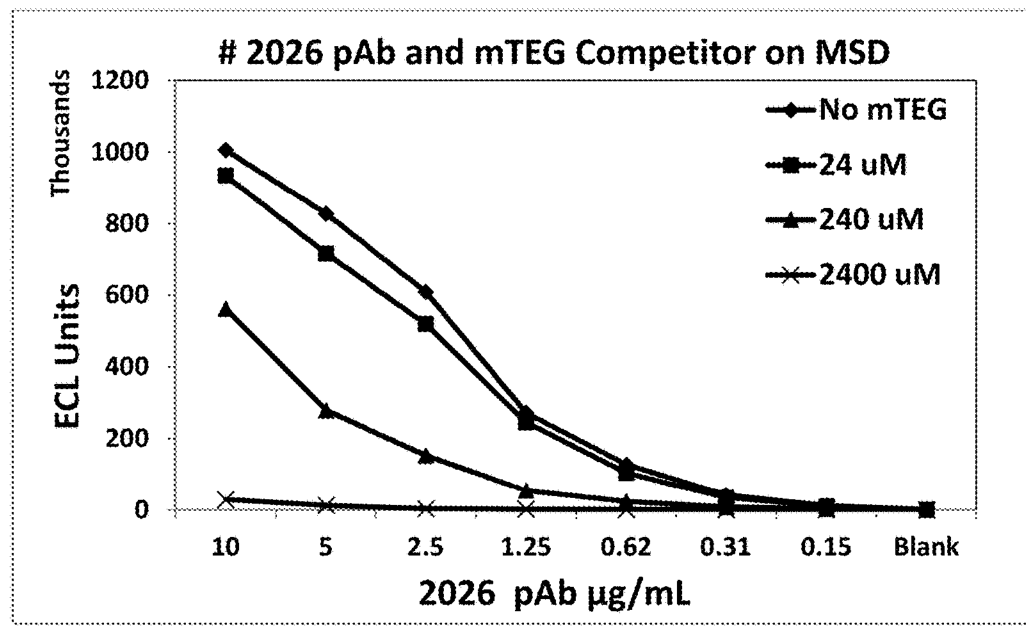
FIGS. 7A and 7B show titrations of anti-PEG pAb 2026 in buffer using direct assay format showing the influence of competitors mTEG and aPEGa, respectively. See Example 8.
Figure 7B:
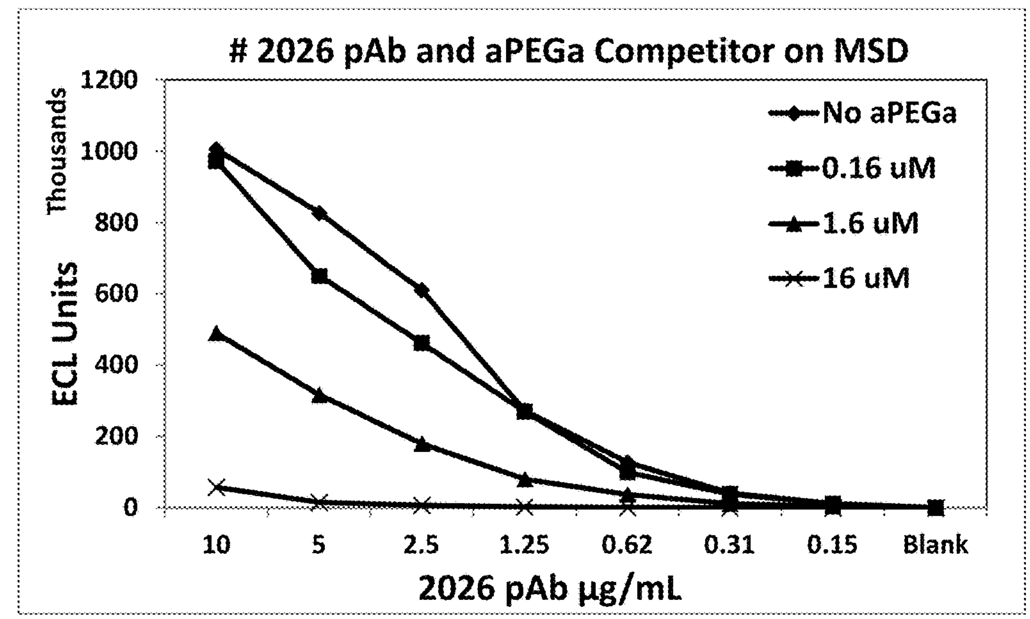
Figure 10A:
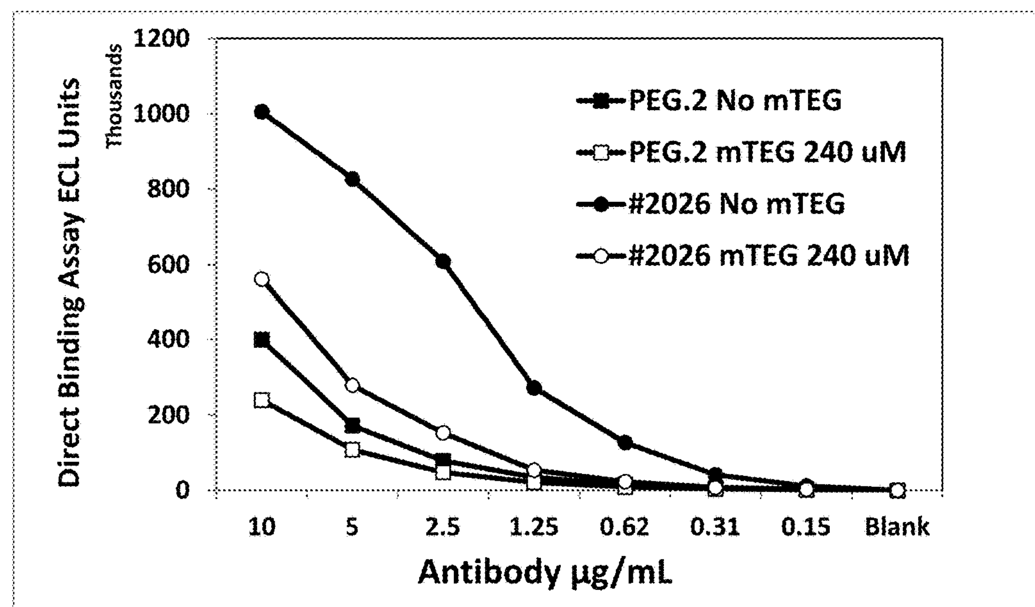
FIGS. 10A and 10B show replots of selected data from FIGS. 6A, 6B, 7A and 7B to facilitate comparison of the influence of competitors mTEG and aPEGa on PEG binding by mAb PEG.2 and pAb 2026. See Example 8.
Figure 10B:
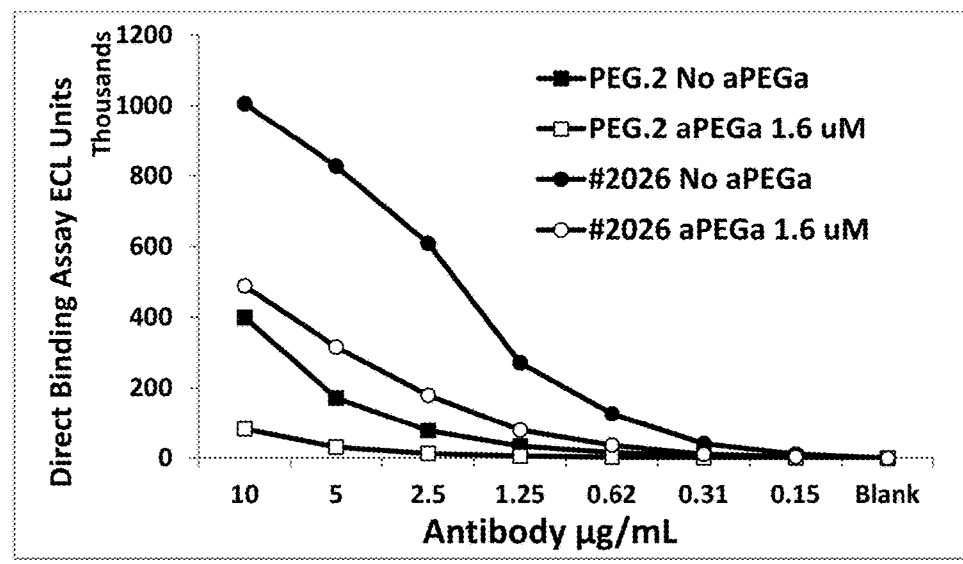

The PEG.2 mAb that had shown preferential binding to larger MW of PEG showed greater inhibition with $H_2N—O—(CH_2CH_2O)_n—NH_2$ than mTEG implying backbone subunit specificity but more dependent on some secondary structure present in the 20 kD $H_2N—O—(CH_2CH_2O)_n—NH_2$ inhibitor. In contrast, the #2026 pAb that had showed preferential binding to smaller to intermediate MW of PEG showed similar inhibition by mTEG and $H_2N—O—(CH_2CH_2O)_n—NH_2$ indicative of its recognition of backbone subunit independent of any possible secondary shapes. The inhibitors thus showed backbone specific antibodies might require some unknown secondary structure in addition to primary repeating units for binding. Results from the semi-homogenous assay (data not shown) corroborated the direct binding assay data (FIGS. 6 and 7) although the direct format demonstrated the inhibition more robustly and at lower inhibitor levels than the semi-homogeneous format. FIG. 10 shows the contrasting inhibition patterns of the two antibodies in the same panel with similar levels of competitor supporting the same conclusion.

In both assay formats, the amount of inhibition increases with the molarity of competitors. At the two highest levels of inhibitor, there is complete suppression of binding for both antibodies suggesting the need to carefully monitor the levels of the PEG reagent in any assay designed to pick up anti-PEG antibodies. The conclusion that PEG.2 mAb is backbone specific and dependent on the secondary structure of PEG was consistent across both assay formats.

TABLE 3

Table of Sequences

| SEQ ID NO. | Description |
|---|---|
| 1 | Antibody PEG.2/6A9 Heavy Chain Variable Domain Nucleic Acid Sequence |
| 2 | Antibody PEG.2/6A9 Heavy Chain Variable Domain Polypeptide Sequence |
| 3 | Antibody PEG.2/6A9 Light Chain Variable Domain Nucleic Acid Sequence |
| 4 | Antibody PEG.2/6A9 Light Chain Variable Domain Polypeptide Sequence |
| 5 | Antibody PEG.1/14B5 Heavy Chain Variable Domain Nucleic Acid Sequence |
| 6 | Antibody PEG.1/14B5 Heavy Chain Variable Domain Polypeptide Sequence |
| 7 | Antibody PEG.1a/14B5 Light Chain Variable Domain a Nucleic Acid Sequence |
| 8 | Antibody PEG.1a/14B5 Light Chain Variable Domain a Polypeptide Sequence |
| 9 | Antibody PEG.1b/14B5 Light Chain Variable Domain b Nucleic Acid Sequence |
| 10 | Antibody PEG.1b/14B5 Light Chain Variable Domain b Polypeptide Sequence |
| 11 | Antibody PEG.2/6A9 Heavy Chain Polypeptide Sequence |
| 12 | Antibody PEG.2/6A9 Light Chain Polypeptide Sequence |
| 13 | Antibody PEG.1/14B5 Heavy Chain Polypeptide Sequence |
| 14 | Antibody PEG.1a/14B5 Light Chain Polypeptide Sequence (Variable Domain a) |

With regard to antibody sequences, the Sequence Listing provides the sequences of the mature variable regions of the heavy and light chains, i.e. the sequences do not include signal peptides.

EQUIVALENTS

Those skilled in the art will recognize, or be able to ascertain using no more than routine experimentation, many equivalents of the specific embodiments disclosed herein. Such equivalents are intended to be encompassed by the following claims.

We claim:

1. A method of detecting human IgG anti-polyethylene glycol (PEG) antibodies in a sample from a human subject comprising:

a. exposing a PEG-coated surface to a sample from a human subject, wherein the sample is blood, serum or any other blood fraction;
b. washing the PEG-coated surface;
c. detecting the presence or absence of human IgG anti-PEG antibodies bound to the PEG-coated surface; and
d. determining the presence, absence, or titer of human IgG anti-PEG antibodies in the sample from a human subject by comparing the results of step c with control experiments using a chimeric anti-PEG antibody comprising:
   i. a non-human variable domain; and
   ii. a human IgG constant domain.

2. The method of claim 1 wherein the chimeric anti-PEG antibody comprises:

a. a heavy chain variable domain comprising:
   i. CDRH1 (residues 31-35 of SEQ ID NO: 2);
   ii. CDRH2 (residues 50-68 of SEQ ID NO: 2); and
   iii. CDRH3 (residues 101-109 of SEQ ID NO: 2) of antibody PEG.2, and b. a light chain variable domain comprising:
i. CDRL1 (residues 31-37 of SEQ ID NO: 4);
ii. CDRL2 (residues 50-56 of SEQ ID NO: 4); and
iii. CDRL3 (residues 89-102 of SEQ ID NO: 4) of antibody PEG.2.

3. The method of claim 1 wherein the chimeric anti-PEG antibody comprises:
a. a heavy chain variable domain comprising:
i. CDRH1 (residues 31-35 of SEQ ID NO: 6);
ii. CDRH2 (residues 50-66 of SEQ ID NO: 6); and
iii. CDRH3 (residues 99-110 of SEQ ID NO: 6) of antibody PEG.1, and
b. a light chain variable domain comprising:
i. CDRL1 (residues 24-34 of SEQ ID NO: 8);
ii. CDRL2 (residues 50-56 of SEQ ID NO: 8); and
iii. CDRL3 (residues 89-102 of SEQ ID NO: 8) of antibody PEG.1a, or
i. CDRL1 (residues 24-39 of SEQ ID NO: 10);
ii. CDRL2 (residues 55-61 of SEQ ID NO: 10); and
iii. CDRL3 (residues 94-102 of SEQ ID NO: 10) of antibody PEG.1b.

4. The method of claim 2 wherein the chimeric anti-PEG antibody comprises heavy and light chain variable domains with at least 95% sequence identity with the heavy and light chain variable domains of antibody PEG.2, wherein antibody PEG.2 comprises:
a. the heavy chain variable domain sequence of SEQ ID NO: 2; and
b. the light chain variable domain sequence of SEQ ID NO: 4;
and wherein the antibody retains the ability to bind to PEG.

5. The method of claim 3 wherein the chimeric anti-PEG antibody comprises heavy and light chain variable domains with at least 95% sequence identity with the heavy and light chain variable domains of antibody PEG.1, wherein antibody PEG.1 comprises:
a. the heavy chain variable domain sequence of SEQ ID NO: 6; and
b. the light chain variable domain sequence of SEQ ID NO: 8 or SEQ ID NO: 10, and wherein the antibody retains the ability to bind to PEG.

6. The method of claim 4 wherein the chimeric anti-PEG antibody comprises:
a. the heavy chain variable domain sequence of SEQ ID NO: 2; and
b. the light chain variable domain sequence of SEQ ID NO: 4.

7. The method of claim 5 wherein the chimeric anti-PEG antibody comprises:
a. the heavy chain variable domain sequence of SEQ ID NO: 6; and
b. the light chain variable domain sequence of SEQ ID NO: 8 or SEQ ID NO: 10.

8. The method of claim 6 wherein the chimeric anti-PEG antibody comprises:
a. the heavy chain sequence of SEQ ID NO: 11; and
b. the light chain sequence of SEQ ID NO: 12.

9. The method of claim 7 wherein the chimeric anti-PEG antibody comprises:
a. the heavy chain sequence of SEQ ID NO: 13; and
b. the light chain sequence of SEQ ID NO: 14.

* * * * *

SEQUENCE LISTING

```
<160> NUMBER OF SEQ ID NOS: 14

<210> SEQ ID NO 1
<211> LENGTH: 360
<212> TYPE: DNA
<213> ORGANISM: Mus musculus

<400> SEQUENCE: 1

gaagtgaagt ttgaggagtc tggaggaggc ttggtgcaac ctggaggatc catgaaactc     60

tcttgtgctg cctctggatt cacttttagt gacgcctgga tggactgggt ccgccagtct    120

ccagagaagg ggcttgagtg ggttgctgaa attagaagca aagctaataa tcatgcaata    180

tattatgctg agtctgtgaa agggaggttc accatctcaa gagatgattc caaaagtagt    240

gtctacctgc aaatgaacag cttaagagct gaagacactg gcatttatta ctgtaccaga    300

ggatggtacc cctactactt tgactactgg ggccaaggca ccactctcac agtctcctca    360


<210> SEQ ID NO 2
<211> LENGTH: 120
<212> TYPE: PRT
<213> ORGANISM: Mus musculus
<220> FEATURE:
<221> NAME/KEY: MISC_FEATURE
<222> LOCATION: (31)..(35)
<223> OTHER INFORMATION: CDRH1
<220> FEATURE:
<221> NAME/KEY: MISC_FEATURE
<222> LOCATION: (50)..(68)
<223> OTHER INFORMATION: CDRH2
<220> FEATURE:
<221> NAME/KEY: MISC_FEATURE
<222> LOCATION: (101)..(109)
<223> OTHER INFORMATION: CDRH3

<400> SEQUENCE: 2

Glu Val Lys Phe Glu Glu Ser Gly Gly Gly Leu Val Gln Pro Gly Gly
1               5                   10                  15

Ser Met Lys Leu Ser Cys Ala Ala Ser Gly Phe Thr Phe Ser Asp Ala
            20                  25                  30

Trp Met Asp Trp Val Arg Gln Ser Pro Glu Lys Gly Leu Glu Trp Val
        35                  40                  45

Ala Glu Ile Arg Ser Lys Ala Asn Asn His Ala Ile Tyr Tyr Ala Glu
    50                  55                  60

Ser Val Lys Gly Arg Phe Thr Ile Ser Arg Asp Asp Ser Lys Ser Ser
65                  70                  75                  80

Val Tyr Leu Gln Met Asn Ser Leu Arg Ala Glu Asp Thr Gly Ile Tyr
                85                  90                  95

Tyr Cys Thr Arg Gly Trp Tyr Pro Tyr Tyr Phe Asp Tyr Trp Gly Gln
            100                 105                 110

Gly Thr Thr Leu Thr Val Ser Ser
        115                 120


<210> SEQ ID NO 3
<211> LENGTH: 336
<212> TYPE: DNA
<213> ORGANISM: Mus musculus

<400> SEQUENCE: 3

gatgttttga tgacccaaac tccactctcc ctgcctgtca gtcttggaga tcaagcctcc     60

atctcttgca gatctagtca gagcattgta catagtgatg gaaacaccta tttagaatgg    120

tacctgcaga aaccaggcca gtctccaaag ctcctgatct acaaagtttc caaccgattt    180
```

```
tctggggtcc cagacaggtt cagtggcagt ggatcaggga cagatttcac actcaagatc    240

agcagagtgg aggctgagga tctgggagtt tattactgct ttcaaggttc acatgttccg    300

tacacgttcg gaggggggac caagctggaa ataaaa                              336


<210> SEQ ID NO 4
<211> LENGTH: 112
<212> TYPE: PRT
<213> ORGANISM: Mus musculus
<220> FEATURE:
<221> NAME/KEY: MISC_FEATURE
<222> LOCATION: (31)..(37)
<223> OTHER INFORMATION: CDRL1
<220> FEATURE:
<221> NAME/KEY: MISC_FEATURE
<222> LOCATION: (50)..(56)
<223> OTHER INFORMATION: CDRL2
<220> FEATURE:
<221> NAME/KEY: MISC_FEATURE
<222> LOCATION: (89)..(102)
<223> OTHER INFORMATION: CDRL3

<400> SEQUENCE: 4

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asp Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110


<210> SEQ ID NO 5
<211> LENGTH: 363
<212> TYPE: DNA
<213> ORGANISM: Mus musculus

<400> SEQUENCE: 5

gaagtgaagc tggtggagtc tgggggaggc ttagtgcagc ctggagggtc cctgaaactc     60

tcctgtgcaa cctctggatt cactttcagt gactattaca tatattgggt tcgccagact    120

ccagagaaga ggctggagtg ggtcgcatcc attagtaatg gtggtggtag cacctattat    180

ccagacactt taaagggccg attcaccatc tccagagaca gtgccaagaa caccctgtac    240

ctgcaaatga gccgtctgaa gtctgaggac acagccatgt attactgtgc aagacaacac    300

gatagtagct acctggcctg gtttgcttac tggggccaag ggactctggt cactgtctct    360

gca                                                                  363


<210> SEQ ID NO 6
<211> LENGTH: 121
<212> TYPE: PRT
<213> ORGANISM: Mus musculus
<220> FEATURE:
<221> NAME/KEY: MISC_FEATURE
<222> LOCATION: (31)..(35)
<223> OTHER INFORMATION: CDRH1
```

```
<220> FEATURE:
<221> NAME/KEY: MISC_FEATURE
<222> LOCATION: (50)..(66)
<223> OTHER INFORMATION: CDRH2
<220> FEATURE:
<221> NAME/KEY: MISC_FEATURE
<222> LOCATION: (99)..(110)
<223> OTHER INFORMATION: CDRH3

<400> SEQUENCE: 6

Glu Val Lys Leu Val Glu Ser Gly Gly Gly Leu Val Gln Pro Gly Gly
1               5                   10                  15

Ser Leu Lys Leu Ser Cys Ala Thr Ser Gly Phe Thr Phe Ser Asp Tyr
            20                  25                  30

Tyr Ile Tyr Trp Val Arg Gln Thr Pro Glu Lys Arg Leu Glu Trp Val
        35                  40                  45

Ala Ser Ile Ser Asn Gly Gly Gly Ser Thr Tyr Tyr Pro Asp Thr Leu
    50                  55                  60

Lys Gly Arg Phe Thr Ile Ser Arg Asp Ser Ala Lys Asn Thr Leu Tyr
65                  70                  75                  80

Leu Gln Met Ser Arg Leu Lys Ser Glu Asp Thr Ala Met Tyr Tyr Cys
                85                  90                  95

Ala Arg Gln His Asp Ser Ser Tyr Leu Ala Trp Phe Ala Tyr Trp Gly
            100                 105                 110

Gln Gly Thr Leu Val Thr Val Ser Ala
        115                 120


<210> SEQ ID NO 7
<211> LENGTH: 336
<212> TYPE: DNA
<213> ORGANISM: Mus musculus

<400> SEQUENCE: 7

gatgttttga tgacccaaac tccactctcc ctgcctgtca gtcttggaga tcaagcctcc      60

atctcttgca gatctagtca gagcattgta catagtaatg gaaacaccta tttagaatgg     120

tacctgcaga aaccaggcca gtctccaaag ctcctgatct acaaagtttc caaccgattt     180

tctggggtcc cagacaggtt cagtggcagt ggatcaggga cagatttcac actcaagatc     240

agcagagtgg aggctgagga tctgggagtt tattactgct ttcaaggttc acatgttcct     300

cccacgttcg gtgctgggac caagctggag ctgaaa                               336


<210> SEQ ID NO 8
<211> LENGTH: 112
<212> TYPE: PRT
<213> ORGANISM: Mus musculus
<220> FEATURE:
<221> NAME/KEY: MISC_FEATURE
<222> LOCATION: (24)..(34)
<223> OTHER INFORMATION: CDRL1
<220> FEATURE:
<221> NAME/KEY: MISC_FEATURE
<222> LOCATION: (50)..(56)
<223> OTHER INFORMATION: CDRL2
<220> FEATURE:
<221> NAME/KEY: MISC_FEATURE
<222> LOCATION: (89)..(102)
<223> OTHER INFORMATION: CDRL3

<400> SEQUENCE: 8

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
```

```
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Pro Thr Phe Gly Ala Gly Thr Lys Leu Glu Leu Lys
            100                 105                 110


<210> SEQ ID NO 9
<211> LENGTH: 336
<212> TYPE: DNA
<213> ORGANISM: Mus musculus

<400> SEQUENCE: 9

gatgttgtga tgacccagac tccactcact ttgtcggtta ccattggaca accagcctct      60

atctcttgca agtcaagtca gagcctctta tatagtaatg gaaaaaccta tttgaattgg     120

ttattacaga ggccaggcca gtctccaaag cgcctaatct atctggtgtc taaactggac     180

tctggagtcc ctgacaggtt cactggcagt ggatcaggaa cagattttac actgaaaatc     240

agcagagtgg aggctgagga tttgggagtt tattactgcg tgcaaggtac acattttccg     300

tggacgttcg gtggaggcac caagctggaa atcaaa                              336


<210> SEQ ID NO 10
<211> LENGTH: 112
<212> TYPE: PRT
<213> ORGANISM: Mus musculus
<220> FEATURE:
<221> NAME/KEY: MISC_FEATURE
<222> LOCATION: (24)..(39)
<223> OTHER INFORMATION: CDRL1
<220> FEATURE:
<221> NAME/KEY: MISC_FEATURE
<222> LOCATION: (55)..(61)
<223> OTHER INFORMATION: CDRL2
<220> FEATURE:
<221> NAME/KEY: MISC_FEATURE
<222> LOCATION: (94)..(102)
<223> OTHER INFORMATION: CDRL3

<400> SEQUENCE: 10

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Tyr Ser
            20                  25                  30

Asn Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Val Gln Gly
                85                  90                  95

Thr His Phe Pro Trp Thr Phe Gly Gly Gly Thr Lys Leu Glu Ile Lys
            100                 105                 110
```

```
<210> SEQ ID NO 11
<211> LENGTH: 449
<212> TYPE: PRT
<213> ORGANISM: Artificial Sequence
<220> FEATURE:
<223> OTHER INFORMATION: Chimeric mAb 6A9/PEG.2 - mouse variable domain
      and human constant domain
<220> FEATURE:
<221> NAME/KEY: MISC_FEATURE
<222> LOCATION: (1)..(120)
<223> OTHER INFORMATION: mouse variable domain
<220> FEATURE:
<221> NAME/KEY: MISC_FEATURE
<222> LOCATION: (31)..(35)
<223> OTHER INFORMATION: CDRH1
<220> FEATURE:
<221> NAME/KEY: MISC_FEATURE
<222> LOCATION: (50)..(68)
<223> OTHER INFORMATION: CDRH2
<220> FEATURE:
<221> NAME/KEY: MISC_FEATURE
<222> LOCATION: (101)..(109)
<223> OTHER INFORMATION: CDRH3
<220> FEATURE:
<221> NAME/KEY: MISC_FEATURE
<222> LOCATION: (121)..(449)
<223> OTHER INFORMATION: human constant domain

<400> SEQUENCE: 11

Glu Val Lys Phe Glu Glu Ser Gly Gly Gly Leu Val Gln Pro Gly Gly
1               5                   10                  15

Ser Met Lys Leu Ser Cys Ala Ala Ser Gly Phe Thr Phe Ser Asp Ala
            20                  25                  30

Trp Met Asp Trp Val Arg Gln Ser Pro Glu Lys Gly Leu Glu Trp Val
        35                  40                  45

Ala Glu Ile Arg Ser Lys Ala Asn Asn His Ala Ile Tyr Tyr Ala Glu
    50                  55                  60

Ser Val Lys Gly Arg Phe Thr Ile Ser Arg Asp Asp Ser Lys Ser Ser
65                  70                  75                  80

Val Tyr Leu Gln Met Asn Ser Leu Arg Ala Glu Asp Thr Gly Ile Tyr
                85                  90                  95

Tyr Cys Thr Arg Gly Trp Tyr Pro Tyr Tyr Phe Asp Tyr Trp Gly Gln
            100                 105                 110

Gly Thr Thr Leu Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
```

```
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly


<210> SEQ ID NO 12
<211> LENGTH: 219
<212> TYPE: PRT
<213> ORGANISM: Artificial Sequence
<220> FEATURE:
<223> OTHER INFORMATION: Chimeric mAb 6A9/PEG.2 - mouse variable domain
      and human constant domain
<220> FEATURE:
<221> NAME/KEY: MISC_FEATURE
<222> LOCATION: (1)..(112)
<223> OTHER INFORMATION: mouse variable domain
<220> FEATURE:
<221> NAME/KEY: MISC_FEATURE
<222> LOCATION: (31)..(37)
<223> OTHER INFORMATION: CDRL1
<220> FEATURE:
<221> NAME/KEY: MISC_FEATURE
<222> LOCATION: (50)..(56)
<223> OTHER INFORMATION: CDRL2
<220> FEATURE:
<221> NAME/KEY: MISC_FEATURE
<222> LOCATION: (89)..(102)
<223> OTHER INFORMATION: CDRL3
<220> FEATURE:
<221> NAME/KEY: MISC_FEATURE
<222> LOCATION: (113)..(219)
<223> OTHER INFORMATION: human constant domain

<400> SEQUENCE: 12

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asp Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60
```

```
Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 13
<211> LENGTH: 450
<212> TYPE: PRT
<213> ORGANISM: Artificial Sequence
<220> FEATURE:
<223> OTHER INFORMATION: Chimeric mAb 14B5/PEG.1 - mouse variable domain
      and human constant domain
<220> FEATURE:
<221> NAME/KEY: MISC_FEATURE
<222> LOCATION: (1)..(121)
<223> OTHER INFORMATION: mouse variable domain
<220> FEATURE:
<221> NAME/KEY: MISC_FEATURE
<222> LOCATION: (31)..(35)
<223> OTHER INFORMATION: CDRH1
<220> FEATURE:
<221> NAME/KEY: MISC_FEATURE
<222> LOCATION: (50)..(66)
<223> OTHER INFORMATION: CDRH2
<220> FEATURE:
<221> NAME/KEY: MISC_FEATURE
<222> LOCATION: (99)..(110)
<223> OTHER INFORMATION: CDRH3
<220> FEATURE:
<221> NAME/KEY: MISC_FEATURE
<222> LOCATION: (122)..(450)
<223> OTHER INFORMATION: human constant domain

<400> SEQUENCE: 13

Glu Val Lys Leu Val Glu Ser Gly Gly Gly Leu Val Gln Pro Gly Gly
1               5                   10                  15

Ser Leu Lys Leu Ser Cys Ala Thr Ser Gly Phe Thr Phe Ser Asp Tyr
            20                  25                  30

Tyr Ile Tyr Trp Val Arg Gln Thr Pro Glu Lys Arg Leu Glu Trp Val
        35                  40                  45

Ala Ser Ile Ser Asn Gly Gly Gly Ser Thr Tyr Tyr Pro Asp Thr Leu
    50                  55                  60

Lys Gly Arg Phe Thr Ile Ser Arg Asp Ser Ala Lys Asn Thr Leu Tyr
65                  70                  75                  80

Leu Gln Met Ser Arg Leu Lys Ser Glu Asp Thr Ala Met Tyr Tyr Cys
                85                  90                  95
```

```
Ala Arg Gln His Asp Ser Ser Tyr Leu Ala Trp Phe Ala Tyr Trp Gly
            100                 105                 110

Gln Gly Thr Leu Val Thr Val Ser Ala Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450
```

<210> SEQ ID NO 14
<211> LENGTH: 219
<212> TYPE: PRT
<213> ORGANISM: Artificial Sequence
<220> FEATURE:
<223> OTHER INFORMATION: Chimeric mAb 14B5/PEG.1 - mouse variable domain and human constant domain
<220> FEATURE:

-continued

```
<221> NAME/KEY: MISC_FEATURE
<222> LOCATION: (1)..(112)
<223> OTHER INFORMATION: mouse variable domain
<220> FEATURE:
<221> NAME/KEY: MISC_FEATURE
<222> LOCATION: (24)..(34)
<223> OTHER INFORMATION: CDRL1
<220> FEATURE:
<221> NAME/KEY: MISC_FEATURE
<222> LOCATION: (50)..(56)
<223> OTHER INFORMATION: CDRL2
<220> FEATURE:
<221> NAME/KEY: MISC_FEATURE
<222> LOCATION: (89)..(102)
<223> OTHER INFORMATION: CDRL3
<220> FEATURE:
<221> NAME/KEY: MISC_FEATURE
<222> LOCATION: (113)..(219)
<223> OTHER INFORMATION: human constant domain

<400> SEQUENCE: 14

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Pro Thr Phe Gly Ala Gly Thr Lys Leu Glu Leu Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```